US008980226B2

(12) United States Patent
Baker et al.

(10) Patent No.: US 8,980,226 B2
(45) Date of Patent: *Mar. 17, 2015

(54) AEROSOLIZED FOSFOMYCIN/AMINOGLYCOSIDE COMBINATION FOR THE TREATMENT OF BACTERIAL RESPIRATORY INFECTIONS

(75) Inventors: William Baker, Bellevue, WA (US); David MacLeod, Issaquah, WA (US)

(73) Assignee: Gilead Sciences, Inc., Foster City, CA (US)

(*) Notice: Subject to any disclaimer, the term of this patent is extended or adjusted under 35 U.S.C. 154(b) by 95 days.

This patent is subject to a terminal disclaimer.

(21) Appl. No.: 13/616,544

(22) Filed: Sep. 14, 2012

(65) Prior Publication Data

US 2013/0071442 A1 Mar. 21, 2013

Related U.S. Application Data

(63) Continuation of application No. 13/085,576, filed on Apr. 13, 2011, now Pat. No. 8,409,549, which is a continuation of application No. 11/596,566, filed as (Continued)

(51) Int. Cl.
*A61K 9/12* (2006.01)
*A61K 9/14* (2006.01)
(Continued)

(52) U.S. Cl.
CPC .......... *A61K 31/7008* (2013.01); *A61K 9/0075* (2013.01); *A61K 9/0078* (2013.01);
(Continued)

(58) Field of Classification Search
None
See application file for complete search history.

(56) References Cited

U.S. PATENT DOCUMENTS 5,454,409 A * 10/1995 McAffer et al. .............. 141/329
5,488,038 A    1/1996 Kondo et al.
(Continued)

FOREIGN PATENT DOCUMENTS

AU    2001283491 B2    1/2002
EP    1750667           1/2011
(Continued)

OTHER PUBLICATIONS

Curran, Barry, et al; "Commercial Mushrooms and Bean Sprouts are a Source of *Pseudomonas aeruginosa*," 2005, ASM; Journal of Clinical Microbiology, vol. 43, No. 11, pp. 5830-5831.*

(Continued)

*Primary Examiner* — Suzanne Ziska
*Assistant Examiner* — Ivan Greene
(74) *Attorney, Agent, or Firm* — Wood, Phillips, Katz, Clark & Mortimer

(57) ABSTRACT

A fosfomycin plus tobramycin combination formulation for delivery by aerosolization is described. The concentrated fosfomycin tobramycin combination formulation containing an efficacious amount of fosfomycin plus tobramycin is able to inhibit susceptible bacteria. Fosfomycin and tobramycin are formulated separately in a dual ampoule such that when reconstituted, the pH is between 4.5 and 8.0 or as a dry powder. The method for treatment of respiratory tract infections by a formulation delivered as an aerosol having mass median aerodynamic diameter predominantly between 1 to 5µ, produced by a jet or ultrasonic nebulizer (or equivalent) or dry powder inhaler.

12 Claims, 21 Drawing Sheets

Time-kill curves for tobramycin alone and 9:1, 8:2, and 7:3 fosfomycin (16 µg/mL): tobramycin (16 µg/mL) combinations against *P. aeruginosa* ATCC 27853.

△ 9:1, ▲ 8:2, ● 7:3, ○ tobramycin, and --- bactericidal line.

Related U.S. Application Data application No. PCT/US2005/014690 on May 2, 2005, now Pat. No. 7,943,118.

(60) Provisional application No. 60/571,739, filed on May 17, 2004, provisional application No. 60/659,005, filed on Mar. 3, 2005.

(51) Int. Cl.
    *A61K 31/7008*  (2006.01)
    *A61K 9/00*     (2006.01)
    *A61K 9/19*     (2006.01)
    *A61K 31/665*   (2006.01)
    *A61K 31/7036*  (2006.01)
    *A61K 45/06*    (2006.01)
    *A61M 11/00*    (2006.01)
    *B65D 85/00*    (2006.01)

(52) U.S. Cl.
    CPC ............... *A61K 9/19* (2013.01); *A61K 31/665* (2013.01); *A61K 31/7036* (2013.01); *A61K 45/06* (2013.01); *A61M 11/00* (2013.01); *A61M 11/005* (2013.01); *B65D 85/00* (2013.01); *Y10S 514/851* (2013.01)
    USPC ................... 424/43; 514/38; 514/40; 514/41; 514/75; 514/99; 514/851; 436/17; 424/45; 424/46

(56) References Cited

U.S. PATENT DOCUMENTS

| | | | |
|---|---|---|---|
| 5,508,269 | A | 4/1996 | Smith et al. |
| 5,618,795 | A | 4/1997 | Kondo et al. |
| 6,083,922 | A | 7/2000 | Montgomery |
| 6,387,886 | B1 | 5/2002 | Montgomery et al. |
| 6,413,946 | B1 | 7/2002 | Niizato et al. |
| 6,440,951 | B1 | 8/2002 | Niizato et al. |
| 6,890,907 | B2 | 5/2005 | Speirs et al. |
| 7,452,524 | B2 | 11/2008 | Hofmann et al. |
| 7,943,118 | B2 * | 5/2011 | Baker et al. ............ 424/43 |
| 8,409,549 | B2 * | 4/2013 | Baker et al. ............ 424/43 |
| 2002/0061281 | A1 * | 5/2002 | Osbakken et al. ........ 424/43 |
| 2002/0187106 | A1 | 12/2002 | Weers et al. |
| 2003/0191051 | A1 | 10/2003 | Needleman et al. |
| 2005/0163722 | A1 | 7/2005 | Malvolti et al. |
| 2006/0062738 | A1 | 3/2006 | Hofmann et al. |
| 2006/0276483 | A1 | 12/2006 | Surber et al. |
| 2007/0196461 | A1 | 8/2007 | Weers |
| 2009/0054374 | A1 | 2/2009 | Kennedy |
| 2010/0113508 | A1 | 5/2010 | Binch et al. |
| 2010/0113509 | A1 | 5/2010 | Binch et al. |
| 2011/0124589 | A1 | 5/2011 | Bhatt et al. |
| 2013/0071442 | A1 | 3/2013 | Baker et al. |

FOREIGN PATENT DOCUMENTS

| | | |
|---|---|---|
| JP | 57-50919 | 3/1982 |
| JP | 58-134028 | 8/1983 |
| JP | 09183730 A | 7/1997 |
| WO | WO 00/35461 | 6/2000 |
| WO | WO 02/03998 | 1/2002 |
| WO | WO 02/074247 A2 | 9/2002 |
| WO | WO 03/035030 A1 | 5/2003 |
| WO | WO 2005/110022 | 11/2005 |
| WO | WO 2008/071197 | 6/2008 |

OTHER PUBLICATIONS

Martinez-Martinez, Luis; Rodriguez, Guadalupe; Pascual, Alvaro; Suarez, Ana Isabel; Perea, Evelio J.; In-vitro activity of antimicrobial agent combinations against multiresistant *Acinetobacter baumannii*; 1996; The British Society for Antimicrobial Chemotherapy; Journal of Antimicrobial Chemotherapy, vol. 38, pp. 1107-1108.*

Nilsson et al., Antimicrobial Agents and Chemotherapy, "Biological Costs and Mechanisms of Fosfomycin Resistance in *Escherichia coti*", Sep. 2003, vol. 47, No. 9 pp. 2850-2858.*

Vakulenko et al., Clinical Microbiology Reviews, "Versatility of Aminoglycosides and Prospects for Their Future", Jul. 2003, vol. 16 No. 3 pp. 430-450.*

Kondo et al., Acta Otolaryngol (Stockh), "Transitional Concentration of Antibacterial Agent to the Maxillary Sinus via a Nebulizer", 1996, Suppl. 525 pp. 64-67.*

Kamijyo et al., Auris Nasus Larynx, "Fosfomycin Nebulizer Therapy to Chronic Sinusitis", 2001,28 pp. 227-232.*

Kastoras et al., "Synergy of fosfomycin with other antibiotics for Gram-positive and Gram-negative bacteria", Eur. J. Clin. Pharmacol, 2010, 66, pp. 359-368.

English translation of a Taiwan Office Action dated Oct. 21, 2010 for corresponding Taiwan Application No. 094115733.

McColley et al., "Fosfomycin/Tobramycin for Inhalation (FTI): Microbiological Results of a Phase 2 Placebo-Controlled Trial in Patients with Cystic Fibrosis and *Pseudomonas aeruginosa*", Poster No. 334 from the 24th Annual North American Cystic Fibrosis Conference, Oct. 21-23, 2010 Baltimore, Maryland.

Tunney "Antimicrobial Activity of Fosfomycin and Tobramycin in Combination Against CF Pathogens Under Aerobic and Anaerobic Conditions", Poster No. 312 from the 24th Annual North American Cystic Fibrosis Conference, Oct. 21-23, 2010 Baltimore, Maryland.

Izumi Hayashi, "The chemotherapy of intractable respiratory tract infection", Current Therapy, Jun. 1988, vol. 6, No. 6, pp. 766-771.

Youichi Hatano, "The influence of medicine on lower respiratory tract", The Journal of Japan Rhinologic Society, 1988, vol. 27, No. 2, pp. 334-336.

Japanese Office Action issued Jun. 14, 2010.

Anwar, H. et al. (1990) "Enhanced Activity of Combination of Tobramycin and Piperacillin for Eradication of Sessile Biofilm Cells of *Pseudomonas aeruginosa*," *Antimicrobial Agents and Chemotherapy* 34(9):1666-1671.

Daza, R. et al. (1977) "Interactions of Fosfomycin with other Antibiotics," *Chemotherapie* 23(Suppl. 1):86-92.

Emerson, J. et al. (2010) "Changes in Cystic Fibrosis Sputum Microbiology in the United States Between 1995 and 2008," *Pediatric Pulmonology* 45:363-370.

Hoiby, N. (2002) "New antimicrobials in the management of cystic fibrosis," *Journal of Antimicrobial Chemotherapy* 49:235-238.

Isenberg, H. et al. (1999) "In Vitro Activity of Ciprofloxacin, Levofloxacin, and Trovafloxacin, Alone and in Combination withβ-Lactams, against Clinical Isolates of *Pseudomonas aeruginosa, Stenotrophomonas maltophilia,* and *Burkholderia cepacia,*" *Diagn Microbiol Infect Dis.* 33:81-86.

Landry, R. et al. (2006) "Mucin-*Pseudomonas aeruginosa* interactions promote biofilm formation and antibiotic resistance," *Molecular Microbiology* 59(1):142-151.

Levy, J. (1983) "Bioactivity of Gentamicin in Purulent Sputum from Patiens with Cystic Fibrosis or Bronchiectasis: Comparison with Activity in Serum," 118:1069-1076.

Levy, J. (1986) Antibiotic Activity in Sputum, *J. Pediatric* 108(2):841-846.

Monurol® Label, Rev. Jul. 2007.

Ohtani, I. et al. (1985) Protective Effect of Fosfomycin against Aminoglycoside Ototoxicity, *ORL* 47:42-48.

Rodriguez-Rojas, A. et al. (2010) "Assessing the Emergence of Resistance: The Absence of Biological Cost In Vivo Compromise Fosfomycin Treatments for *P. aeruginosa* Infections," *PLoS ONE* www.plosone.org 5(4): e10193.doi:10/1371/journal.pone.0010193.

Tobi® Label Rev. Jul. 2008, Printed in USA 5001770.

Vishwanath, S. et al. (1987) "Effects of subminimal inhibitory concentration of antibodies on the adherence of *Pseudomonas aeruginosa* to tracheobronchial mucin," *Journal of Antimicrobial Chemotherapy* 19:579-583.

Yanagihara, K. et al. (2000) "Combination therapy for chronic *Pseudomonas aeruginosa* respiratory infection associated with biofilm formation," *Journal of Antimicrobial Chemotherapy* 46:69-72.

(56) References Cited

OTHER PUBLICATIONS

Yassien, M. el al. (1995) "Modulation of Biofilms of *Pseudomonas aeruginosa* by Quinolones," Antimicrobial Agents and Chemotherapy 39(10):2262-2268.
Aaron, "Antibiotic synergy testing should not be routine for patients with cystic fibrosis who are infected with multiresistant bacterial organisms", Pediatric Respiratory Reviews (2007) 8, pp. 256-261.
Borowski et al., "Studies on the combined action of phosphonomycin with streptomycin, penicillin G and ampicillin", Archivum Immunologiae et Therapiae Experimentalis 1976, 24, pp. 191-195.
Borowski et al., "Combined action of fosfomycin with β-Lactam and aminoglycoside antibiotics", Chemotherapy 23 (Suppl. 1): 1977, pp. 82-85.
Bugnon et al., "Bactericidal effect of pefloxacin and fosfomycin against *Pseudomonas aeruginosa* in a rabbit endocarditis model with pharmacokinetics of pefloxacin in humans simulated in vivo", Eur. J. Clin. Microbiol. Infect. Dis., 1997, 16, pp. 575-580.
Buisson et al., "[Preliminary study of the antagonistic effects between fosfomycin and beta-lactams on *Pseudomonas aeruginosa* observed on the antibiogram]"Pathyol Biol. (Paris), Jun. 1988; 36 (5 Pt 2): 671-4.
Chin et al., "Synergy of fosfomycin with beta-lactam antibiotics against *Staphylococci* and aerobic gram-negative bacilli", Drugs Exptl. Clin. Res. XII(12) 1986, pp. 943-947.
Dubrous et al., "[Sensitivity to fosfomycin of multiresistant serotype 012 *Pseudomonas aeruginosa*. Multicenter study]", Pathol. Biol. (Paris), Jun. 1997; 45(6), 472-8.
Eliopoulos et al., "Antibiotic combinations: should they be tested?", Clinical Microbiology Reviews, Apr. 1988, vol. 1, No. 2 pp. 139-156.
Ferrara et al., "Effect of different combinations of sparfloxacin, oxacillin, and fosfomycin against methicillin-resistant *Staphylococci*", Eur. Journal Clin. Microbiol. Infect. Dis., vol. 16, 1997 Notes pp. 535-537.
Figueredo et al., "Synergy of ciprofloxacin with fosfomycin in vitro against *Pseudomonas* isolates from patients with cystic fibrosis", Journal of Antimicrobial Chemotherapy, 1988 22, pp. 41-50.
Hayami et al., "Activities of β-lactams, fluoroquinolones, amikacin and fosfomycin alone and in combination against *Pseudomonas aeruginosa* isolated from complicated urinary tract infections", J. Infect Chemother. 1999 5, pp. 130-138.
Hunt et al., "Macromolecular mechanisms of sputum inhibition of tobramycin activity", Antimicrobial Agents and Chemotherapy, Jan. 1995, vol. 39, No. 1, pp. 34-39.
Kasai et al., "Synergistic effects of a macrolide and a cell wall-affecting antibiotic on *Pseudomonas aeruginosa* in vitro and in vivo", The Journal of Antibiotics, Jul. 1982, vol. XXXV, No. 7, pp. 858-865.
Kono et al., "Combined therapy with arbekacin and fosfomycin for methicillin-resistant *Staphylococcus aureus* infections", The Japanese Journal of Antibiotics 47-6, Jun. 1994, 798, pp. 238-243.
Kumon et al., "Combination effect of fosfomycin and ofloxacin against *Pseudomonas aeruginosa* growing in a biofilm", Antimicrobial Agents and Chemotherapy, May 1995, vol. 39, No. 5, pp. 1038-1044.
Lorian, "Antimicrobial Combinations", Antibiotics in Laboratory Medicine, Fifth Edition, pp. 370-382.
MacLeod et al., "Antibacterial activities of a fosfomycin/tobramycin combination: a novel inhaled antibiotic for bronchiectasis", Journal of Antimicrobial Chemotherapy, Aug. 13, 2009, pp. 1-8.
Martinez et al., "In-vitro activity of antimicrobial agent combinations against multiresistant *Acinetobacter baumannii*" Journal of Antimicrobial Chemotherapy, 1996 38, pp. 1107-1108.
Mendelman et al., "Aminoglycoside penetration, inactivation, and efficacy in cystic fibrosis sputum", Am. Rev. Respir. Dis., 1985, 132, pp. 761-765.
Miksza-Zylkiewicz et al., "Combined action of phosphomycin with streptomycin and gentamicin", Archivum Immununologiae et Therapiae Experimentalis, 1977, 23, pp. 741-747.
Monden et al., "Role of fosfomycin in a synergistic combination with ofloxacin against *Pseudomonas aeruginosa* in a biofilm",J. Infect. Chemother. 2002, 8, pp. 218-226.
Morikawa et al., "Synergistic effect of fosfomycin and arbekacin on a methicillin-resistant *Staphylococcus aureus*-induced biofilm in a rat model", International Journal of Antimicrobial Agents 25, 2005, pp. 44-50.
Nakazawa et al., "Enhancement of antimicrobial effects of various antibiotics against methicillin-resistant *Staphylococcus aureus* (MRSA) by combination with fosfomycin", J. Infect. Chemother. 2003, 9, pp. 304-309.
Neu et al., "Synergy of fosmidomycin (FR-31564) and other antimicrobial agents", Antimicrobial Agents and Chemotherapy, Oct. 1982, vol. 22, No. 4, pp. 560-563.
Niida et al., "[Studies on the combined effect of fosfomycin with sulbactam/cefoperazone on methicillin-resistant *Staphylococcus aureus* and *Pseudomonas aeruginosa*]", Jpn. J. Antibiot., Jan. 1994, 47(1), pp. 1.
Novelli et al., "Clinicalo Chemotherapeutic evaluation of fosfomycin plus amoxicillin (co-fosfolactamine): a prospective double-blind clinical trial", Chemioterapia, Oct. 1984, vol. III, No. 5, pp. 281-285.
Pestel et al., "In vitro interactions between different β-lactam antibiotics and fosfomycin against bloodstream isolates of *Enterococci*", Antimicrobial Agents and Chemotherapy, Oct. 1995, vol. 39, No. 10, pp. 2341-2344.
Quentin et al., [In vitro action of fosfomycin combined with refampicin, pefloxacin and imipenem on *Staphylococci* (checkerboard method in a liquid medium)], Pathol. Biol. (Paris), Feb. 1987, 3.5(2), pp. 1.
Ramphal et al., "The binding of anti-pseudomonal antibiotics to macromolecules from cystic fibrosis sputum", Journal of Antimicrobial Chemotherapy, 1988, 22, pp. 483-490.
Rodriguez et al., "Single- and combination-antibiotic therapy for experimental endocarditis caused by methicillin-resistant *Staphylococcus aureus*", Antimicrobial Agents and Chemotherapy, Sep. 1987, vol. 31, No. 9, pp. 1444-1445.
Rodriguez et al., "Experimental endocarditis and fosfomycin", Drugs Exptl. Clin. Res., 1985, XI(1), pp. 55-62.
Russo et al., "[Synergic action of the combination of fosfomycin and kanendomycin against gram-positive and gram-negative bacteria]", Ann Scalvo., Jan.-Feb. 1980, 22(1), pp. 1.
Saggers et al., "Some observations on the penetration of antibiotics through mucus in vitro", J. Clin. Path., 1966, 19, pp. 313-317.
Tanaka et al., [Staggered intensive chemotherapy using arbekacin fosfomycin and ceftazidime on polymicrobial infections involving MRSA], Jpn. J. Antibiot., Jun. 1994, 47(6), pp. 1.
Tsuda et al., "[Clinical evaluation of imipenem/cilastatin sodium and fosfomycin as second-line combination chemotherapy in severe infections associated with hematologic disorders]", Jpn. J. Antibiot., Feb. 1993, 46(2), pp. 1-2.
Ullmann et al., "In vitro investigations on the action of fosfomycin alone and in combination with other antibiotics on *Pseudomonas aeruginosa* and *Serratia marcescens*", Arzneim.-Forscyh/Drug Res., 1980, 30(II), Nr. 8, pp. 1247-1249.
Uno, "[Combination effect of fosfomycin otic solution and norfloxacin against chronic otitis media]", Kansenshogaku Zasshi. Apr. 1999, 73(4), pp. 1.
Utsui et al., "Antibacterials activity of cefmetazole alone and in combination with fosfomycin against methicillin- and cephem-resistant *Staphylococcus aureus*", Antimicrobial Agents and Chemotherapy, Dec. 1986, vol. 30, No. 6, pp. 917-922.
Watine et al., "Susceptibility of multiresistant serotype 012 *Pseudomonas aeruginosa* to fosfomycin in combination with other antibiotics", Pathologie Biologie Apr. 1994, vol. 42, No. 4, pp. 293-295.
Xu et al., "Effects of erythromycin and fosfomycin on *Pseudomonas aeruginosa* biofilm in vitro", Zhonghua Jie He He Hu Xi Za Zhi., Jun. 2001, 24(6), pp. 1.
Zeitlinger et al., "Target site bacterial killing of cefpirome and fosfomycin in critically ill patients", International Journal of Antimicrobial Agents 21, 2003, pp. 562-567.

(56) References Cited

OTHER PUBLICATIONS

MacLeod et al., "Antibacterial Activities of a Fosfomycin: Tobramycin Combination (GS-9310/11) Against Pathogens Commonly Found in CF and Bronchiectasis", Poster No. 328, 21$^{st}$ Annual North American Cystic Fibrosis Conference, Oct. 3-6, 2007, Anaheim, California.
Al-Aloul et al., Pediatric Pulmonology, "Renal Impairment in Cystic Fibrosis Patients Due to Repeated Intravenous Aminoglycoside Use", 2005, 39 pp. 15-20.
Ansorg et al., Chemotherapy, "Comparison of Inhibitory and Bactericidal Activity of Antipseudomonal Antibiotics Against *Pseudomonas aeruginosa* Isolates from Cystic Fibrosis Patients", 1990, 36 pp. 222-229.
Arca et al., Journal of Antimicrobial Chemotherapy, "Plasmid-encoded Fosfomycin Resistance in Bacteria Isolated from the Urinary Tract in a Multicentre Survey", 1997, 40 pp. 393-399.
Bacardi et al., Chemotherapy, "Treatment of Respiratory Infections with Fosfomycin", 1977, 23 pp. 343-347.
Bonora et al., Chemotherapy, "Fosfomycin in Treatment of Respiratory Bacterial Infections", 1977, 23 pp. 337-341.
Conway, Chronic Respiratory Disease, "Review Series: Practical Management of Cystic Fibrosis Nebulized Antibiotic Therapy: the Evidence", 2005, 2 pp. 35-41.
Conway et al., Am. J. Respir. Med. "Antibiotic Treatment of Multidrug-Resistant Organisms in Cystic Fibrosis", 2003, 2(4) pp. 321-332.
Craig, Clinical Infectious Diseases", Pharmacokinetic/Pharmacodynamic Parameters: Rationale for Antibacterial Dosing of Mice and Men", 1998, 26 pp. 1-12.
Conway et al., European Respiratory Journal, "Antibiotic Therapy Against *Pseudomonas aeruginosa* in Cystic Fibrosis: a European Consensus", 2000, 16 pp. 749-767.
Flume et al., Pharmacotherapy, "The Rationale for Aerosolized Antibiotics", 2002, 22(3pt. 2) pp. 71S-79S.
Forsgren et al., Journal of Antimicrobial Chemotherapy, "Antimicrobial Activity of Fosfomycin in Vitro", 1983, 11 pp. 467-471.
Geller et al., American College of Chest Physicians, "Pharmacokinetics and Bioavailability of Aerosolized Tobramycin in Cystic Fibrosis", 2002, 122 pp. 219-226.
Gibson et al., American Journal of Crit. Care Med., "Pathophysiology and Management of Pulmonary Infections in Cystic Fibrosis", 2003, vol. 168 pp. 918-951.
Greenwood et al., Infection, "The Influence of Anaerobiosis on the Activity of Fosfomycin Trometamol", 1992, 20 Suppl. 4 pp. S 305-S 309.
Grif et al., The Journal of Antimicrobial Chemotherapy, "In Vitro Activity of Fosfomycin in Combination with Various Antistaphylococcal Substances", Aug. 2001, vol. 48(2) pp. 209-217.
Grimm, Infection, "In Vitro Investigations with Fosfomycin on Mueller-Hinton Agar with and Without Glucose-6-Phosphate", 1979, 7 No. 5 pp. 256-259.
Hammett-Stabler et al., Clinical Chemistry, "Laboratory Guidelines for Monitoring of Antimicrobial Drugs", 1998, 44:5 pp. 1129-1140.
Honorato et al., Chemotherapy, "Fosfomycin in Acute Bronchopneumopathies", 1977, 23 (Suppl. 1) pp. 331-336.
Hunt et al., Antimicrobial Agents and Chemotherapy, "Macromolecular Mechanisms of Sputum Inhibition of Tobramycin Activity", Jan. 1995, vol. 39, No. 1 pp. 34-39.
Kahan et al., Annals. New York Academy of Sciences, "The Mechanism of Action of Fosfomycin (Phosphonomycin)", 1974, 253 pp. 364-386.
Kamijyo et al., Auris Nasus Larynx, "Fosfomycin Nebulizer Therapy to Chronic Sinusitis", 2001, 28 pp. 227-232.
Katznelson et al., Correspondence, "Fosfomycin in the Treatment of Cystic Fibrosis", vol. 3 No. 3 p. 213.
Kuhn, American College of Chest Physicians, "Formulation of Aerosolized Therapeutics", 2001, 120 pp. 94-98.

Lang et al., American Journal of Crit Care Med. "Multiple Combination Bactericidal Antibiotic Testing for Patients with Cystic Fibrosis Infected with Multiresistant Strains of *Pseudomonas aeruginosa*", 2000, vol. 162 pp. 2241-2245.
Marchese et al., International Journal of Antimicrobial Agents, "In Vitro Activity of Fosfomycin Against Gram-Negative Urinary Pathogens and the Biological Cost of Fosfomycin Resistance", 2003, 22 pp. S53-S59.
Mendelman et al., Am. Rev. Respir. Dis. "Aminoglycoside Penetration, Inactivation, and Efficacy in Cystic Fibrosis Sputum$^{1-3}$" 1985, 132 pp. 761-765.
Menendez et al., Chemotherapy, "Treatment of Respiratory Infections with Fosfomycin", 1977, 23 (Suppl. 1)348-357.
Barry et al., NCCLS, "Methods for Determining Bactericidal Activity of Antimicrobial Agents; Approved Guideline", Sep. 1999, M26-A vol. 19 No. 18 Replaces M26-T vol. 12 No. 9, 50 pages.
Ferraro et al., NCCLS, "Methods for Dilution Antimicrobial Susceptibility Test for Bacteria That Grow Aerobically; Approved Standard—Sixth Edition", Jan. 2003, M7-A6, vol. 23 No. 2 Replaces M7-A5, vol. 20 No. 2, 75 pages.
Mingeot-Leclerco et al., Antimicrobial Agents and Chemotherapy, "Aminoglycosides: Nephrotoxicity", May 1999, vol. 43, No. 5 pp. 1003-1012.
Mirakhur et al., Journal of Cystic Fibrosis, "Fosfomycin Therapy for Multiresistant *Pseudomonas aeruginosa* in Cystic Fibrosis", 2003, 2 pp. 19-24.
Moreno et al., Unidad de Enfermedades Infecciosas, Servicio de Microbiologia, Centro Especial Ramon y Cajal, "Cure of a Case of *Haemophilus aphrophilus* Endocarditis with a Combination of Fosfomycin and Gentamicin", pp. 771-772.
Mueller et al., Antimicrobial Agents and Chemotherapy, "Issues in Pharmacokinetics of Anti-Infective Agents: Kill Curves versus MIC", Feb. 2004, vol. 48, No. 2 pp. 369-377.
Wikler et al., NCCLS, "Performance Standards for Antimicrobial Susceptibility Testing; Fourteenth Informational Supplement", Jan. 2004, M100-S14 vol. 24, No. 1 Replaces M100-S13, 164 pages.
Nilsson et al., Antimicrobial Agents and Chemotherapy, "Biological Costs and Mechanisms of Fosfomycin Resistance in *Escherichia coli*", Sep. 2003, vol. 47, No. 9 pp. 2850-2858.
Okazaki et al., J. Infect. Chemotherapy, "Effectiveness of Fosfomycin Combined with Other Antimicrobial Agents Against Multi-resistant *Pseudomonas aeruginosa* Isolates Using the Efficacy Time Index Assay", XP-002430612, 2002 8 pp. 37-42.
O'Riordan, Respiratory Care, "Inhaled Antimicrobial Therapy: From Cystic Fibrosis to the Flu", 2000, vol. 45 No. 7 pp. 836-845.
Perri et al., Diagnostic Microbiology and Infectious Disease, "In Vitro Susceptibility of Vancomycin-resistant *Enterococci* (VRE) to Fosfomycin", 2002 42, pp. 269-271.
Pitt et al., Thorax Online, "Survey of Resistance of *Pseudomonas aeruginosa* from UK Patients with Cystic Fibrosis to Six Commonly Prescribed Antimicrobial Agents", 2003, 58 pp. 794-796.
Ramphal et al., Journal of Antimicrobial Chemotherapy, "The Binding of Anti-*Pseudomonal* Antibiotics to Macromolecules from Cystic Fibrosis Sputum", 1988, 22 pp. 483-490.
Ramsey et al., The New England Journal of Medicine, "Efficacy of Aerosolized Tobramycin in Patients with Cystic Fibrosis", Jun. 17, 1993, vol. 328 No. 24 pp. 1740-1746.
Ramsey, The New England Journal of Medicine, "Management of Pulmonary Disease in Patients with Cystic Fibrosis", Jul. 18, 1996, vol. 335 No. 3 pp. 179-188.
Ramsey et al., The New England Journal of Medicine, "Intermittent Administration of Inhaled Tobramycin in Patients with Cystic Fibrosis", Jan. 7, 1999, vol. 340 No. 1, pp. 23-30.
Reeves, Journal of Antimicrobial Chemotherapy, "Fosfomycin Trometamol", 1994, 34 pp. 853-858.
Schulin, The Journal of Antimicrobial Chemotherapy, "In Vitro Activity of the Aerosolized Agents Colistin and Tobramycin and Five Intravenous Agents Against *Pseudomonas aeruginosa* Isolated from Cystic Fibrosis Patients in Southwestern Germany", Feb. 2002, vol. 49(2) pp. 403-406.

(56) References Cited

OTHER PUBLICATIONS

Shawar et al., Antimicrobial Agents and Chemotherapy, "Activities of Tobramycin and Six Other Antibiotics Against *Pseudomonas aeruginosa* Isolates from Patients with Cystic Fibrosis", Dec. 1999, vol. 43 No. 12 pp. 2877-2880.
Smith et al., The Journal of Pediatrics, "Comparison of a β-lactam Alone Versus β-lactam and an Aminoglycoside for Pulmonary Exacerbation in Cystic Fibrosis", Apr. 1999, vol. 134 No. 4 pp. 413-421.
Spencker et al., Clinical Microbiol. Infect., "Development of Resistance in *Pseudomonas aeruginosa* Obtained from Patients with Cystic Fibrosis at Different Times", 2003, 9 pp. 370-379.
Takahashi et al., Antimicrobial Agents and Chemotherapy, "Synergistic Activities of Combinations of β-Lactams, Fosfomycin, and Tobramycin Against *Pseudomonas aeruginosa*", Nov. 1984, vol. 26 No. 5 pp. 789-791.
Tan et al., Am Journal of Respir. Crit. Care Med., "Aminoglycoside Prescribing and Surveillance in Cystic Fibrosis", 2003, vol. 167 pp. 819-823.
Tessier et al., European Journal of Microbiol. Infect. Dis., "In Vitro Activity of Fosfomycin Combined with Ceftazidime, Combined with Ceftazidime, Imipenem, Amikacin, and Ciprofloxacin Against *Pseudomonas aeruginosa*", XP-002433919, 1997, vol. 16 pp. 159-162.
Touw et al., European Respiratory Journal, "Inhalation of Antibiotics in Cystic Fibrosis", XP-002430615, 1995, 8 pp. 1594-1604.
Eldere, The Journal of Antimicrobial Chemotherapy, "Multicentre Surveillance of *Pseudomonas aeruginosa* Susceptibility Patterns in Nosocomial Infections", Feb. 2003, vol. 51(2) pp. 347-352.
Weiss et al., Antimicrobial Agents and Chemotherapy, "Routine Susceptibility Testing of Four Antibiotic Combinations for Improvement of Laboratory Guide to Therapy of Cystic Fibrosis Infections Caused by *Pseudomonas aeruginosa*", Nov. 1995, vol. 39 No. 11 pp. 2411-2414.
Woodruff et al., Chemotherapy, "Fosfomycin: Laboratory Studies", 1977, 23 (Suppl. 1) pp. 1-22.
Bendiak et al., (2009) "The Approach to *Pseudomonas aeruginosa* in Cystic Fibrosis", *Semin Respir Crit Care Med*, 30(5): 587-595.
ClinicalTrials.gov, ClinicalTrials.gov Identifier NCT00739648, (Last Updated 2010) "A Phase 2 Study of MP-376 to Prevent Acute Exacerbations in Chronic Obstructive Pulmonary Disease(COPD) Patients".
Doring et al. (2000) "Antibiotic Therapy Against *Pseudomonas aeruginosa* in Cystic Fibrosis: a European Consensus", European Respiratory Journal, 16:749-767.
International Search Report for PCT/US2010/056256 Dated Apr. 13, 2011.
International Search Report for PCT/US2012/036260.
Joukhadar et al., (2003), "Target site penetration of fosfomycin in critically il patients", *J. Antimicrob. Chemother.*, 51 (5): 1247-1252.
King, P, et al., (2006) "Bronchiectasis", *Internal Medicine Journal*, vol. 36 (11) 729-737.
Konstan et al., Safety, efficacy and convenience of tobramycin inhalation powder in cystic fibrosis patients: The EAGER trial, J. Cyst. Fibr., (2010), pp. 54-61.
Lucas P. et al., "Enhancement of small prticle size dry powder aerosol formulations using a ultra low density addivie", Pharmaceutical Research, vol. 16, No. 10, Dec. 31, 1999, pp. 1643-1647.
National Heart Lung and Blood Institute information on cystic fibrosis, retrieved from <www.nhlbi.nih.gov/health/dci/Diseases/cf> on Sep. 11, 2010, pp. 1-11.
Patel I, et al., (2004), "Bronchiectasis, exacerbation indices, and inflammation in chronic obstructive pulmonary disease" *American Journal of Respiratory and Critical Care Medicine*, vol. 170 (4): 400-407.
Sethi, S, et al (2008) "Infection in the Pathogenesis and Course of Chronic Obstructive Pulmonary Disease" *N. Eng J Med*, 359:2355-65.
Sibley, C. et al., (2009), "The relevance of the polymicrobial nature of airway infection in the acute and chronic management of patients with cystic fibrosis" *Current Opinion in Investigational Drugs*, 10 (8): 787-794.
Sykes, A et al., (2007) "Diagnosis of pathogens in exacerbations of chronic obstructive pulmonary disease", *Proceedings of the American Thoracic Society*, vol. 4 (8) 642-646.
The Cystic Fibrosis Foundation Frequently Asked Questions about cystic fibrosis, retrieved from <www.cff.org/AboutCF/Faqs> on Sep. 11, 2010, pp. 1-5.
US Department of Health and Human Services, Food and Drug Administration, Center for Drug Evaluation and Research (CDER) (Aug. 2008), Clinical Antimicrobial, Revision 1, Guidance for Industry—"Acute Bacterial Exacerbations of Chronic Bronchitis in Patients with Chronic Obstructive Pulmonary Disease: Developing Antimicrobial Drugs for Treatment".
Velayudhan, J, et al (2010) "The Protein Encoded by the *Pseudomonas aeruginosa* PA01 Gene, PA1549, is a Putative Cation-Transportin ATPase With a Role in Tobramycin Uptake" *AM J Respir Crit Care Med*, 181:A4742.

\* cited by examiner

Time-kill curves for a 9:1 fosfomycin:tobramycin combination against

*P. aeruginosa* ATCC 27853.

△ no drug control, ▲ fosfomycin (28.8 µg/mL), ● tobramycin (3.2 µg/mL), ■ fosfomycin (28.8 µg/mL) + tobramycin (3.2 µg/mL), and --- bactericidal line.

Time-kill curves for a 9:1 fosfomycin:tobramycin combination against

*P. aeruginosa* ATCC 27853.

△ no drug control, ▲ fosfomycin (14.4 μg/mL), ● tobramycin (1.6 μg/mL), ■ fosfomycin (14.4 μg/mL) + tobramycin (1.6 μg/mL), and --- bactericidal line.

Time-kill curves for a 8:2 fosfomycin:tobramycin combination against *P. aeruginosa* ATCC 27853.

△ no drug control, ▲ fosfomycin (25.6 μg/mL), ● tobramycin (6.4 μg/mL), ■ fosfomycin (25.6 μg/mL) + tobramycin (6.4 μg/mL), and --- bactericidal line.

Time-kill curves for a 8:2 fosfomycin:tobramycin combination against
*P. aeruginosa* ATCC 27853.

△ no drug control, ▲ fosfomycin (12.8 μg/mL), ● tobramycin (3.2 μg/mL), ■ fosfomycin (12.8 μg/mL) + tobramycin (3.2 μg/mL), and --- bactericidal line.

Time-kill curves for a 7:3 fosfomycin:tobramycin combination against

*P. aeruginosa* ATCC 27853.

△ no drug control, ▲ fosfomycin (22.4 μg/mL), ● tobramycin (9.6 μg/mL), ■ fosfomycin (22.4 μg/mL) + tobramycin (9.6 μg/mL), and --- bactericidal line.

Time-kill curves for a 7:3 fosfomycin:tobramycin combination against

*P. aeruginosa* ATCC 27853.

△ no drug control, ▲ fosfomycin (11.2 µg/mL), ● tobramycin (4.8 µg/mL), ■ fosfomycin (11.2 µg/mL) + tobramycin (4.8 µg/mL), and --- bactericidal line.

Time-kill curves for a 7:3 fosfomycin:tobramycin combination against

*P. aeruginosa* ATCC 27853.

Δ no drug control, ▲ fosfomycin (5.6 µg/mL), ● tobramycin (2.4 µg/mL), ■ fosfomycin (5.6 µg/mL) + tobramycin (2.4 µg/mL), and --- bactericidal line.

Time-kill curves for tobramycin alone and 9:1, 8:2, and 7:3 fosfomycin (32 μg/mL): tobramycin (32 μg/mL) combinations against *P. aeruginosa* ATCC 27853.

Δ 9:1, ▲ 8:2, ● 7:3, ○ tobramycin, and --- bactericidal line.

Time-kill curves for tobramycin alone and 9:1, 8:2, and 7:3 fosfomycin (16 μg/mL): tobramycin (16 μg/mL) combinations against *P. aeruginosa* ATCC 27853.

Δ 9:1, ▲ 8:2, ● 7:3, ○ tobramycin, and --- bactericidal line.

Time-kill curves for a 9:1 fosfomycin:tobramycin combination against

*P. aeruginosa* ATCC 27853.

Δ no drug control, □ 4.0 μg/mL, ▨ 8.0 μg/mL, ○ 16 μg/mL, ● 32 μg/mL, and --- bactericidal line.

Time-kill curves for a 8:2 fosfomycin:tobramycin combination against
*P. aeruginosa* ATCC 27853.

△ no drug control, □ 4.0 μg/mL, ■ 8.0 μg/mL, ○ 16 μg/mL, ● 32 μg/mL, and --- bactericidal line.

Time-kill curves for a 7:3 fosfomycin:tobramycin combination against

*P. aeruginosa* ATCC 27853.

△ no drug control, □ 4.0 µg/mL, ▨ 8.0 µg/mL, ○ 16 µg/mL, ● 32 µg/mL, and --- bactericidal line.

Killing of *E. coli* in the rat lung 31.1 mg/mL solution of a 9:1 fosfomycin:tobramycin combination.

Killing of *E. coli* in the rat lung 31.1 mg/mL solution of a 8:2 fosfomycin:tobramycin combination.

Killing of *E. coli* in the rat lung 31.1 mg/mL solution of a 7:3 fosfomycin:tobramycin combination.

Killing of *E. coli* in the rat lung 31.1 mg/mL solution of a 9:1 fosfomycin tobramycin combination (F9:T1)
28 mg/mL solution of a fosfomycin alone (F9)
Rats were exposed to aerosolized antibiotic for 1 hour, twice daily for 3 days.

Killing of *E. coli* in the rat lung 31.1 mg/mL solution of a 9:1 fosfomycin tobramycin combination (F9:T1)
3.1 mg/mL solution of tobramycin alone (T1)
Rats were exposed to aerosolized antibiotic for 1 hour, twice daily for 3 days.

Killing of *E. coli* in the rat lung 31.1 mg/mL solution of a 8:2 fosfomycin:tobramycin combination (F8:T2)
40 mg/mL solution of tobramycin
Rats were exposed to aerosolized antibiotic for 1 hour, twice daily for 3 days.

Killing of *P. aeruginosa* in the rat lung 31.1 mg/mL solution of a 8:2 fosfomycin:tobramycin combination (F8:T2)
8.2 mg/mL solution of fosfomycin alone (F8)
Rats were exposed to aerosolized antibiotic for 1 hour, twice daily for 3 days.

Killing of *P. aeruginosa* in the rat lung 31.1 mg/mL solution of a 8:2 fosfomycin:tobramycin combination (F8:T2)
6.2 mg/mL solution of tobramycin alone (T2)
Rats were exposed to aerosolized antibiotic for 1 hour, twice daily for 3 days.

Killing of *P. aeruginosa* in the rat lung after 60 mg/mL solution of a 8:2 fosfomycin:tobramycin combination
90 mg/mL solution of a 8:2 fosfomycin:tobramycin
Rats were exposed to aerosolized antibiotic for 1 hour, twice daily for 3 days.

AEROSOLIZED FOSFOMYCIN/AMINOGLYCOSIDE COMBINATION FOR THE TREATMENT OF BACTERIAL RESPIRATORY INFECTIONS

CROSS-REFERENCE TO RELATED APPLICATION

This application is a continuation of U.S. application Ser. No. 13/085,576, filed Apr. 13, 2011, now U.S. Pat. No. 8,409,549, which is a continuation of U.S. application Ser. No. 11/596,566, filed Nov. 15, 2006, which is the U.S. National Stage of International Application No. PCT/US2005/014690 filed May 2, 2005, now U.S. Pat. No. 7,943,118, which claims priority of U.S. Provisional Applications 60/571,739 filed May 17, 2004 and 60/659,005 filed Mar. 3, 2005, the disclosure of which is incorporated herein by reference.

FIELD OF THE INVENTION

The current invention concerns a novel, safe, nonirritating and physiologically compatible inhalable fosfomycin plus aminoglycoside combination formulation suitable for treatment of respiratory bacterial infections caused by Gram-negative bacteria, such as *Burkholderia cepacia, Citrobacter* species, *Escherichia coli, Enterobacter* species, *Fusobacterium* species, *Haemophilus influenzae, Klebsiella pneumoniae, Klebsiella oxytoca, Moraxella catarrhalis, Proteus mirabilis, Prevotella* species, *Pseudomonas aeruginosa, Serratia marcescens, Stenotrophomonas maltophilia, Alcaligenes xylosoxidans,* and Gram-positive bacteria, such as methicillin-resistant *Staphylococcus aureus,* methicillin-sensitive *Staphylococcus aureus, Streptococcus pneumoniae,* and β-hemolytic *Streptococcus* species.

BACKGROUND OF THE INVENTION

The most widely accepted therapy for treating respiratory infections caused by Gram-negative bacteria in cystic fibrosis patients involves intravenous administration of a single antibiotic or combinations of antibiotics (Gibson et al., 2003; Ramsey, 1996). This method of treatment has several significant limitations including: (1) narrow spectrum of activity of existing antibiotics, (2) insufficient concentrations of antibiotic reaching the respiratory tract to ensure rapid onset and high rates of bacterial killing, and (3) development of adverse side affects due to high systemic concentrations of drug.

Aerosol administration of antibiotics (Conway, 2005; O'Riordan, 2000) addresses several of the limitations of parenteral administration (Flume and Klepser, 2002; Kuhn, 2001). It enables topical delivery of high concentrations of drug to the endobronchial spaces and reduces side effects by lowering systemic exposure to antibiotic. However, cystic fibrosis patients typically receive prolonged and repeated antibiotic therapies over the entire duration of their adult lives (Gibson et al., 2003; Ramsey, 1996). Therefore, cumulative aminoglycoside toxicity and development of resistance remains a significant problem.

Fosfomycin

Fosfomycin is a broad spectrum phosphonic acid antibiotic (Kahan et. al., 1974; Woodruff et al., 1977) that has bactericidal activity against Gram-negative bacteria including *Citrobacter* spp., *E. coli, Enterobacter* spp., *K. pneumoniae, P. aeruginosa, Salmonella* spp., *Shigella* spp., and *S. marcescens* (Greenwood et. al., 1992; Grimm, 1979; Marchese et. al., 2003; Schulin, 2002), as well as Gram-positive bacteria including vancomycin resistant enterococci, methicillin-resistant *S. aureus* (MRSA), methicillin-sensitive *S. aureus* (MSSA), and *S. pneumoniae* (Greenwood et. al., 1992; Grimm, 1979; Perri et. al., 2002). Fosfomycin has the greatest activity against *E. coli, Proteus* spp., *Salmonella* spp., *Shigella* spp., and *S. marcescens* which are generally inhibited at fosfomycin concentrations ≤64 µg/mL (Forsgren and Walder, 1983). Fosfomycin is moderately active against *P. aeruginosa* (Forsgren and Walder, 1983), particularly when compared to tobramycin (Schulin, 2002).

Fosfomycin is bactericidal but exhibits time-dependent killing against *E. coli* and *S. aureus* (Grif et al., 2001). The rate and degree of killing depends on the length of time fosfomycin is in contact with the target organism (Craig, 1998; Mueller et al., 2004). Increasing the fosfomycin concentration will not produce a corresponding increase in the rate or degree of killing activity. This feature is significant because it is preferable to treat *P. aeruginosa* infections with antibiotics that exhibit bactericidal, concentration-dependent killing activity (Craig, 1998; Mueller et. al., 2004).

Fosfomycin monotherapy is commonly used in the treatment of uncomplicated urinary tract infections caused by *E. coli,* and less frequently in treating bacterial respiratory infections including in patients with cystic fibrosis (Kamijyo et al., 2001; Katznelson et al., 1984; Kondo et al., 1996; Reeves, 1994; Bacardi et al., 1977; Bonora et al., 1977; Honorato et al., 1977; Menendez et al., 1977). However, fosfomycin alone has not been widely used to treat infections caused by *P. aeruginosa.* Fosfomycin has been administered parenterally in combination with antibiotics of different classes to treat endocarditis (Moreno, et. al., 1986) and cystic fibrosis (Mirakhur et. al., 2003) but has not been delivered directly to the lung environment by aerosol administration.

Fosfomycin is available in both oral (fosfomycin calcium and fosfomycin trometamol) and intravenous (fosfomycin disodium) formulations (Woodruff et al., 1977). Fosfomycin trometamol is the preferred formulation for oral administration because it is more readily absorbed into the blood compared to fosfomycin calcium. Following a single intravenous or intramuscular dose of 2 g of fosfomycin, peak serum concentrations range between 25-95 µg/mL within 1-2 hours (Woodruff et al., 1977). By comparison, concentrations reach 1-13 µg/mL in normal lung after parenteral administration of a comparable dose of fosfomycin (Bonora et al., 1977) which is an insufficient to kill most bacterial pathogens, in particular *P. aeruginosa* (Forsgren and Walder, 1983; Schulin, 2002). Patients with cystic fibrosis have altered pharmacokinetics characterized by an increased volume of distribution and rate of clearance (Tan et al., 2003), which would likely further decrease the efficacy of parenterally administered fosfomycin.

Fosfomycin is widely distributed in various body tissues and fluids but does not significantly bind to plasma proteins (Mirakhur et al., 2003). Consequently, fosfomycin is available to exert antibacterial effects if it reaches sufficient concentrations at the site of infection. The respiratory tract of cystic fibrosis patients are obstructed with viscous secretions called sputum (Ramsey, 1996). The effectiveness of several classes of antibiotics such as aminoglycosides and β-lactams is reduced due to poor penetration into sputum. Additionally, the activity of these antibiotics is further reduced by binding to sputum components (Hunt et al., 1995; Kuhn, 2001; Ramphal et al., 1988; Mendelman et al., 1985).

Development of resistance in bacteria isolated from patients treated with fosfomycin for urinary tract infections occurs very infrequently (Marchese et al., 2003). Cross-resistance with other classes of cell wall inhibiting antibiotics does not occur because fosfomycin acts on the enzyme phosphoenolpyruvate (UDP-N-acetylglucosamine enolpyruvaltransferase) which is not targeted by other antibiotics (Kahan et al., 1974; Woodruff et al., 1977). Fosfomycin is actively taken up into bacterial cells by two transport systems; a constitutively functional L-α-glycerophosphate transport and the hexose-phosphate uptake system (Kahan et al., 1974). When fosfomycin resistance occurs, it is typically due to a genetic mutation in one or both of the chromosomally encoded transport systems, and less commonly by modifying enzymes (Area et al., 1997; Nilsson et al., 2003).

Tobramycin.

Tobramycin is an aminoglycoside antibiotic that is active against Gram-negative aerobic bacilli including *P. aeruginosa, E. coli, Acinetobacter* spp., *Citrobacter* spp., *Enterobacter* spp., *K. pneumoniae, Proteus* spp., *Salmonella* spp., *S. marcescens*, and *Shigella* spp (Vakulenko and Mobashery, 2003). In particular, tobramycin is highly active against *P. aeruginosa*. The tobramycin MICs of susceptible *P. aeruginosa* are typically less than 2 µg/mL (Shawar et al., 1999; Spencker et al., 2002; Van Eldere, 2003). Most Gram-positive bacteria are resistant to tobramycin, with the exception of *S. aureus* and *S. epidermidis* (Vakulenko and Mobashery, 2003).

Tobramycin is rapidly bactericidal and exhibits concentration-dependent killing (Vakulenko and Mobashery, 2003). Increasing the tobramycin concentration increases both the rate and extent of bacterial killing. Therefore, to achieve therapeutic success, it is necessary to administer a large enough dose to produce a peak tobramycin level 5-10 times greater than the MIC of the target organism at the site of infection. It is preferable to treat *P. aeruginosa* infections with antibiotics that exhibit bactericidal, concentration-dependent killing activity (Ansorg et al., 1990).

Tobramycin is usually administered to treat less serious Gram-negative bacterial infections (Vakulenko and Mobashery, 2003). However, it may be combined with other classes of antibiotics to treat severe infections of the urinary tract and abdomen, as well as endocarditis and bacteremia (Vakulenko and Mobashery, 2003). Parenteral administration of tobramycin in combination with cell-wall inhibiting antibiotics has been used to treat respiratory infections, in particular those caused by *P. aeruginosa* in CF patients (Gibson et al., 2003; Lang et al., 2000; Ramsey et al., 1999; Ramsey et al., 1993; Smith et al., 1999; Spencker et al., 2003).

Tobramycin is poorly absorbed orally and must be administered parenterally (Hammett-Stabler and Johns, 1998). Tobramycin is available in both intravenous and aerosol formulations. After parenteral administration, tobramycin is primarily distributed within the extracellular fluid. Tobramycin is rapidly excreted by glomular filtration resulting in a plasma half-life of 1-2 hours (Tan et al., 2003). Penetration of tobramycin into respiratory secretions is very poor and its activity is further reduced by binding to sputum (Kuhn, 2001). Aerosol administration of tobramycin results in significantly higher sputum levels of ≥1000 µg/mL (Geller et al., 2002) compared with parenteral administration, but sputum binding remains a significant problem (Hunt et al., 1995; Mendelman et al., 1985; Ramphal et al., 1988).

Nephrotoxicity and ototoxicity are adverse reactions associated with tobramycin therapy (Al-Aloui et al., 2005; Hammett-Stabler and Johns, 1998). Nephrotoxicity results from accumulation of tobramycin within lysosomes of epithelial cells lining the proximal tubules. This causes an alteration of cell function and ultimately cell necrosis (Mingeot-Leclercq and Tulkens, 1999). Clinically, this presents as nonoliguric renal failure. The prevalence of nephrotoxicity in cystic fibrosis patients is estimated to be 31-42% (Al-Aloui et al., 2005). The incidence of ototoxicity, which is characterized by loss of hearing and dizziness, is estimated to be as high as 25% of patients treated with aminoglycosides (Hammett-Stabler and Johns, 1998). Unlike nephrotoxicity, ototoxicity is irreversible. The greatest risk factor for the development of toxicity is cumulative exposure to large doses of tobramycin (Hammett-Stabler and Johns, 1998; Mingeot-Leclercq and Tulkens, 1999). Cystic fibrosis patients are treated with prolonged and repeated high-dosages of tobramycin over their entire lifetime (Tan et al., 2003) and are at increased risk of developing cumulative renal failure (Al-Aloui et al., 2005).

Bacterial resistance to tobramycin has become increasingly prevalent and is due to repeated and prolonged antibiotic monotherapy (Conway et al., 2003; Van Eldere, 2003; Mirakhur et al., 2003; Pitt et al., 2005; Schulin, 2002). For example, Cystic fibrosis patients are colonized with *P. aeruginosa* strains which are largely resistant to tobramycin gentamicin, ceftazidime, piperacillin, and ciprofloxacin (Eldere, 2003; Pitt et al., 2005; Pitt et al., 2003; Weiss and Lapointe, 1995). Thus, existing antibiotic therapies are becoming ineffective for treating *P. aeruginosa* infections because of drug resistance.

It is clear that there is a continued need for an improved method of treatment for acute and chronic respiratory infections caused by Gram-negative and Gram-positive bacteria, particularly multidrug resistant *P. aeruginosa*. This is particularly evident in cystic fibrosis patients where current therapies are limited by problems with development of resistance and toxicity. Such method of treatment would preferably comprise inhalation of an aerosolized antibiotic combination of fosfomycin and an aminoglycoside such as tobramycin that delivers a therapeutically effective amount of the drugs directly to the endobronchial space of the airways or to the nasal passages. Such treatment would be efficacious, reduce the frequency of drug resistance, and improve safety.

It would be highly advantageous to provide a formulation and system for delivery of a sufficient dose of fosfomycin plus an aminoglycoside such as tobramycin in a concentrated form, containing the smallest possible volume of solution or weight of dry powder which can be aerosolized and delivered predominantly to the endobronchial space.

Thus, it is an objective of this invention to provide a concentrated liquid or dry powder formulation of fosfomycin plus aminoglycoside which contains sufficient but not excessive amounts of fosfomycin and aminoglycoside which can be efficiently aerosolized by nebulization into aerosol particles sizes predominantly within a range of 1 to 5 um and having salinity that is adjusted to permit generation of a fosfomycin plus aminoglycoside aerosol well tolerated by patients, and which has an adequate shelf live.

SUMMARY OF THE INVENTION

One aspect of this invention is a method for treatment of upper respiratory tract infections like bacterial sinusitis and lower respiratory tract (pulmonary) infections like cystic fibrosis, chronic pulmonary *Pseudomonas* infection in cystic fibrosis patients, *Pseudomonas* infections after first infection, bronchiectasis, hospital and community acquired pneumonia, and ventilator associated pneumonia (VAP) caused by Gram-negative and Gram-positive bacteria comprising the step of administering an effective amount of an aerosol formulation comprising fosfomycin and tobramycin into the endobronchial or nasal space of patients in need of such treatment.

Another aspect of the current invention is a concentrated formulation either liquid or dry powder, suitable for delivery of a fosfomycin tobramycin combination into the endobronchial or nasal space of patients to treat lower and upper respiratory bacterial infections.

Still another aspect of the current invention is a formulation, either liquid or dry powder, suitable for delivery of aminoglycoside and fosfomycin into the endobronchial and nasal space of patients that reduces the development of antibiotic resistance compared to either drug used alone.

Still another aspect of the current invention is a formulation, either liquid or dry powder, suitable for delivery of an aminoglycoside and fosfomycin into the endobronchial or nasal space of patients that increases the post antibiotic affect (PAE) compared to the PAE of either the drug used alone.

Still another aspect of the current invention is a formulation comprising from 1-300 mg of fosfomycin and from 1 to 300 mg aminoglycoside in 0.5 to 7 mL of water with a chloride concentration >30 mM wherein said formulation has a pH between 4.5 and 8.0 and is delivered by aerosolization. The aerosol contains particles that have a mass median aerodynamic diameter (MMAD) predominantly between 1 to 5μ, and is administered using a nebulizer able to atomize the particles of the required size.

Still another aspect of the current invention is a dry powder formulation comprising from about 1 to about 300 mg of fosfomycin, from about 1 to about 300 mg aminoglycoside and at least one pharmaceutically acceptable excipient in a micronized dry powder form that delivers particles with a MMAD of 1 and 5μ upon aerosolization.

The invention concerns an inhalable formulation comprising fosfomycin plus an aminoglycoside suitable for treatment of acute and chronic pulmonary bacterial infections, particularly those caused by the multidrug resistant Gram-negative bacteria *P. aeruginosa* which are resistant to treatment with β-lactams and aminoglycosides. The aerosol formulation has a small volume yet delivers a therapeutically efficacious dose of fosfomycin plus aminoglycoside to the site of infection in amounts sufficient to treat bacterial respiratory infections. The dry powder and reconstituted aminoglycoside plus fosfomycin formulations have a long shelf-life and storage stability.

The formulations of the present invention preferably comprise from 5 to 9 parts by weight fosfomycin and 1 to 5 parts by weight aminoglycoside, preferably from about 7 to 9 parts by weight fosfomycin and 1 to 3 parts by weight aminoglycoside and more preferably about 8 parts by weight fosfomycin and about 2 parts by weight aminoglycoside. The most preferred aminoglycoside is tobramycin.

DEFINITION OF TERMS

Figure 1:
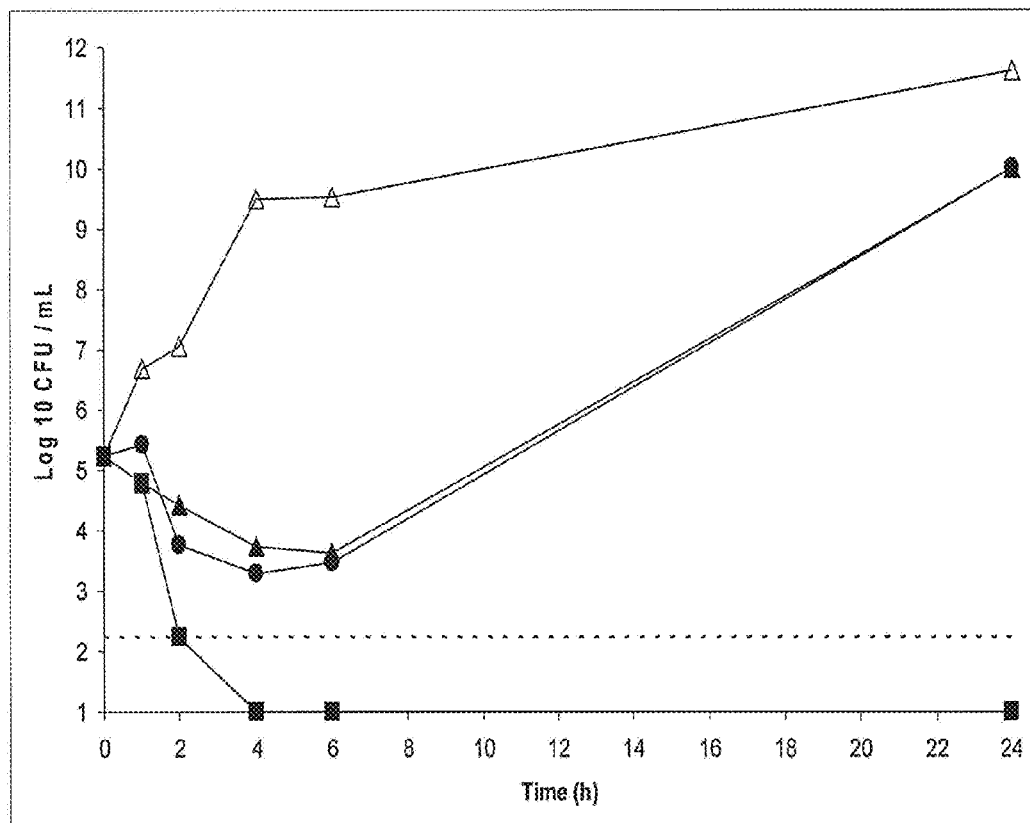
FIGS. 1 and 2 show time-kill curves for a 9:1 fosfomycin:tobramycin combination and demonstrate rapid bactericidal killing of *P. aeruginosa* ATCC 27853 compared to bacteriostatic killing of fosfomycin and tobramycin alone.

As used herein:

"Quarter normal saline" or "¼ NS" means normal saline diluted to its quarter strength containing 0.225% (w/v) NaCl.

"9:1 fosfomycin:tobramycin" means a water solution or dry powder formulation containing a 9:1 ratio by weight of fosfomycin acid to tobramycin base.

"8:2 fosfomycin:tobramycin" means a water solution or dry powder formulation containing a 8:2 ratio by weight of fosfomycin acid to tobramycin base such that the amount of fosfomycin is four times the amount of tobramycin.

"7:3 fosfomycin:tobramycin" means a water solution or dry powder formulation containing a 7:3 ratio by weight of fosfomycin acid to tobramycin base.

"5:5 fosfomycin:tobramycin" means a water solution or dry powder formulation containing a 5:5 ratio by weight of fosfomycin acid to tobramycin base.

"Minimal inhibitory concentration (MIC)" means the lowest concentration of antibiotic (s) that prevents visible growth after incubation for 18-20 hours at 35° C.

"Minimal bactericidal concentration (MBC)" means the lowest concentration of antibiotic that results in ≥3 $Log_{10}$ of bacterial killing.

"Time-dependent killing" means higher drug concentrations do not kill bacteria any faster or to a greater extent.

"Concentration-dependent killing" means the higher the drug concentration, the greater the rate and extent of bacterial killing.

"Bacteriostatic" means the antibiotic acts by inhibiting bacterial growth.

"Bactericidal" means the antibiotics acts by killing bacteria.

"Synergy" means the combined effect of the antibiotics being examined is significantly greater than either drug alone.

DETAILED DESCRIPTION OF THE PREFERRED EMBODIMENT

The current invention concerns a concentrated fosfomycin plus tobramycin formulation suitable for efficacious delivery by aerosolization into the endobronchial or nasal space. The invention is preferably suitable for formulation of concentrated fosfomycin plus tobramycin for aerosolization by jet, ultrasonic, or equivalent nebulizers to produce aerosol particles between 1 and 5µ necessary for the efficacious delivery of fosfomycin plus tobramycin into the endobronchial or nasal space to treat bacterial infections, particularly those caused by multidrug-resistant *Pseudomonas aeruginosa*. The formulation contains a minimal yet efficacious amount of fosfomycin plus tobramycin formulated in the smallest possible volume of physiologically acceptable solution having a salinity adjusted to permit generation of a fosfomycin and tobramycin aerosol well tolerated by patients but minimizing the development of secondary undesirable side effects such as bronchospasm and cough.

Primary requirements for any aerosolized formulation are its safety and efficacy. Additional advantages are lower cost, practicality of use, long shelf-life, storage and manipulation of nebulizer.

Aerosolized fosfomycin plus tobramycin is formulated for efficacious delivery of fosfomycin plus tobramycin to the lung endobronchial or nasal space. A nebulizer is selected to allow the formation of a fosfomycin plus tobramycin aerosol having a mass median aerodynamic diameter predominantly between 1 to 5µ. The formulated and delivered amount of fosfomycin plus tobramycin is efficacious for the treatment of bacterial pulmonary infections, particularly those caused by multi-drug resistant *Pseudomonas aeruginosa*. The formulation has salinity, osmotic strength, and pH adjusted to permit generation of a fosfomycin plus tobramycin aerosol that is well tolerated by patients. The formulation has the smallest possible aerosolizable volume able to deliver an effective dose of fosfomycin plus tobramycin to the site of the infection. Additionally, the aerosolized formulation does not impair the functionality of the airways or nasal passages and minimizes undesirable side effects.

I. Evaluation of the Antibiotic Combinations

Fosfomycin:aminoglycosides combinations were formulated as described in Example 1. Fosfomycin comprised the major component of the combination because of it's inherent safety and the need to reduce the toxicity of the aminoglycoside. The fosfomycin: aminoglycoside combinations, in particular fosfomycin:tobramycin were evaluated for (a.) in vitro potency, (b.) killing rates, (c.) frequency of resistance, and (d.) animal efficacy.

a. In Vitro Potency

The in vitro potency of fosfomycin and tobramycin alone and in combination against a panel of Gram-negative and Gram-positive bacteria representative of species that cause respiratory tract infections in cystic fibrosis, bronchiectasis, sinusitis and ventilator-associated pneumoniae is shown in Tables 1 and 2. The data show that the fosfomycin:tobramycin combinations have antibacterial activity against a broad spectrum of Gram-positive and Gram-negative bacteria. The MICs of the fosfomycin:tobramycin combinations did not improve over fosfomycin or tobramycin alone.

TABLE 1

MIC values of fosfomycin and tobramycin alone and in combination against Gram-negative bacteria.

| Bacteria | MIC (µg/mL) | | | | |
|---|---|---|---|---|---|
| | Fosfomycin | Tobramycin | F9:T1 | F7:T3 | F5:T5 |
| *P. aeruginosa* | | | | | |
| COR-003 | 16 | 0.5 | 8 | 4 | 1 |
| COR-009 | 1024 | 2048 | 1024 | 512 | 2048 |
| COR-021 | 8 | 64 | 8 | 8 | 8 |
| COR-027 | 128 | 0.5 | 8 | 2 | 1 |

TABLE 1-continued

MIC values of fosfomycin and tobramycin alone and in combination against Gram-negative bacteria.

| Bacteria | MIC (µg/mL) | | | | |
|---|---|---|---|---|---|
| | Fosfomycin | Tobramycin | F9:T1 | F7:T3 | F5:T5 |
| *E. coli* | | | | | |
| COR-032 | 1 | 0.5 | 1 | 1 | 1 |
| COR-039 | 64 | 0.25 | 2 | 0.5 | 0.5 |
| COR-040 | 1 | 32 | 1 | 1 | 2 |
| *H. influenzae* | | | | | |
| COR-042 | 8 | 0.5 | 4 | 2 | 1 |
| COR-049 | 128 | 0.5 | 4 | 1 | 1 |
| *B. cepacia* | | | | | |
| COR-090 | ≥2048 | 128 | 1024 | ND | ND |
| COR-098 | ≥2048 | 64 | 1024 | ND | ND |
| *S. maltophilia* | | | | | |
| COR-082 | 128 | 4 | 4 | 4 | 8 |
| COR-083 | 64 | 512 | 256 | 128 | 128 |
| COR-087 | ≥512 | 128 | 128 | 128 | 128 |
| *K. pneumoniae* | | | | | |
| COR-042 | 8 | 0.5 | 4 | 2 | 1 |
| COR-049 | 128 | 0.5 | 4 | 1 | 1 |
| *M. catarrhalis* | | | | | |
| COR-109 | 4 | 8 | 4 | ND | ND |
| COR-113 | 4 | 8 | 4 | ND | ND |

ND = Not determined.

TABLE 2

MIC values of fosfomycin and tobramycin alone and in combination against Gram-positive bacteria.

| Bacteria | MIC (µg/mL) | | | | |
|---|---|---|---|---|---|
| | Fosfomycin | Tobramycin | F9:T1 | F7:T3 | F5:T5 |
| *S. aureus* | | | | | |
| COR-051 (MSSA) | 1 | 0.25 | 2 | 1 | 0.5 |
| COR-055 (MRSA) | 4 | 0.25 | 4 | 1 | 0.5 |
| COR-059 | 2 | 128 | 2 | 4 | 4 |
| COR-060 (GISA) | 2 | 64 | 1 | 4 | 8 |
| *S. pneumoniae* | | | | | |
| COR-061 | 32 | 64 | 16 | 32 | 32 |
| COR-068 | 8 | 16 | 16 | 16 | 16 |
| *S. pyogenes* | | | | | |
| COR-104 | 64 | 32 | ND | ND | ND |
| COR-105 | 16 | 64 | ND | ND | ND |
| *E. faecalis* | | | | | |
| COR-099 | 32 | 512 | ND | ND | ND |
| COR-103 | 32 | 8 | ND | ND | ND |

ND = Not determined

Table 3 shows the $MIC_{50}$ and $MIC_{90}$ values of fosfomycin and tobramycin alone and in combination for 100 *P. aeruginosa* strains isolated from lung sputum samples from cystic fibrosis patients. This study demonstrated that in the absence of mucin, tobramycin was the most active antibiotic. Combining fosfomycin and tobramycin resulted in a significant improvement in the $MIC_{50}$ and $MIC_{90}$ values compared to fosfomycin alone. In the CF mucin binding model (+mucin), the fosfomycin:tobramycin combinations had MIC$_{50}$ and MIC$_{90}$ values to comparable tobramycin alone.

TABLE 3

MIC values of fosfomycin and tobramycin alone and in combination for 100 *P. aeruginosa* strains.

| Antibiotic | MIC$_{50}$ (µg/mL) | | MIC$_{90}$ (µg/mL) | |
|---|---|---|---|---|
| | Mucin (−) | Mucin (+) | Mucin (−) | Mucin (+) |
| Fosfomycin | 64 | 64 | ≥512 | 128 |
| Tobramycin | 2 | 16 | 16 | 64 |
| F9:T1 | 16 | 32 | 64 | 128 |
| F8:T2 | 8 | 32 | 64 | 128 |
| F7:T3 | 8 | 16 | 64 | 64 |

Table 4 shows the results of checkerboard synergy studies between fosfomycin and nine aminoglycosides. The interactions between the nine different fosfomycin:aminoglycoside combinations were all classified as indifferent. None of the combinations had synergistic activity against *P. aeruginosa* ATCC 27853. This data demonstrates it is not obvious that an improvement in efficacy would be achieved by combining fosfomycin and aminoglycosides.

TABLE 4

Checkerboard studies between fosfomycin and various aminoglycosides for *P. aeruginosa* ATCC 27853.

| Antibiotic Combination | Interaction |
|---|---|
| Fosfomycin:Tobramycin | Indifferent |
| Fosfomycin:Gentamicin | Indifferent |
| Fosfomycin:Arbekacin | Indifferent |
| Fosfomycin:Dibekacin | Indifferent |
| Fosfomycin:Kanamycin B | Indifferent |
| Fosfomycin:Streptomycin | Indifferent |
| Fosfomycin:Amikacin | Indifferent |
| Fosfomycin:Neomycin | Indifferent |
| Fosfomycin:Netilmicin | Indifferent |

Table 5 shows the results of checkerboard synergy studies between fosfomycin and tobramycin against clinical strains of *P. aeruginosa*, *E. coli*, *H. influenzae*, and *S. aureus*. Interactions between fosfomycin and tobramycin were classified as indifferent for the vast majority of isolates examined. The interaction between fosfomycin and tobramycin combination was synergistic against only one strain of *P. aeruginosa* and one strain of *E. coli*. This data further suggests it was not obvious that an improvement in efficacy would be achieved by combining fosfomycin and tobramycin.

TABLE 5

Checkerboard studies between fosfomycin and tobramycin for *P. aeruginosa*, *E. coli*, *H. influenzae*, and *S. aureus* strains.

| Bacterial Strains | N = | Antibiotic Interaction | | | |
|---|---|---|---|---|---|
| | | Synergism | Addition | Indifference | Antagonism |
| *P. aeruginosa* | 17 | 1 | 0 | 16 | 0 |
| *E. coli* | 5 | 1 | 0 | 4 | 0 |
| *H influenzae* | 1 | 0 | 0 | 1 | 0 |
| *S. aureus* | 4 | 0 | 0 | 4 | 0 |

Table 6 shows the MBC/MIC values of fosfomycin and tobramycin alone and 9:1, 8:2, and 7:3 fosfomycin:tobramycin combinations for *P. aeruginosa* ATCC 27853. Antibiotics with MBC/MIC values ≤1 are preferable because they inhibit bacteria by killing rather slowing growth. This study unexpectedly demonstrated the MBC/MIC values of the 9:1, 8:2, and 7:3 fosfomycin:tobramycin combinations were identical to tobramycin alone. This finding was unexpected since the fosfomycin alone MBC/MIC ratio was ≥8. The study also showed that a similar finding was not observed with any of the other fosfomycin: aminoglycoside combinations.

TABLE 6

MBC/MIC values of aminoglycosides alone and 9:1, 8:2, and 7:3 combinations of fosfomycin and aminoglycoside for *P. aeruginosa* ATCC 27853.

| Antibiotic Combination | MBC/MIC | | | |
|---|---|---|---|---|
| | Aminoglycoside | F9:A1 | F8:A2 | F7:A3 |
| Fosfomycin:Tobramycin | 1 | 1 | 1 | 1 |
| Fosfomycin:Gentamicin | 2 | 4 | 2 | 8 |
| Fosfomycin:Amikacin | 2 | 4 | 4 | 2 |
| Fosfomycin:Netilimicin | 1 | 2 | 4 | 2 |
| Fosfomycin:Arbekacin | 1 | 4 | 4 | 2 |
| Fosfomycin:Streptomycin | 4 | 2 | 2 | 2 |
| Fosfomycin:Neomycin | 2 | 2 | 2 | 4 |
| Fosfomycin:Kanamycin B | ND | 4 | 2 | 4 |
| Fosfomycin:Dibekacin | 1 | 4 | 2 | 1 |

ND = Not determined.
"F" = Fosfomycin and "A" = aminoglycoside

Table 7 shows the MBC/MIC values of fosfomycin and tobramycin alone and 9:1, 8:2, and 7:3 combinations for *P. aeruginosa* ATCC 27853, *E. coli* ATCC 25922, and *S. aureus* ATCC 29213. For *P. aeruginosa*, the MBC/MIC values of the 9:1, 8:2, and 7:3 combinations were identical to tobramycin alone. This finding was unexpected since it was not observed with *E. coli* or *S. aureus*.

TABLE 7

MBC/MIC values of fosfomycin and tobramycin alone and 9:1, 8:2, and 7:3 combinations of fosfomycin and tobramycin.

| Antibiotic | MBC/MIC | | |
|---|---|---|---|
| | *P. aeruginosa* | *E. coli* | *S. aureus* |
| Fosfomycin | ≥8 | 8 | 1 |
| Tobramycin | 1 | 1 | 8 |
| F9:T1 | 1 | 1 | 2 |
| F8:T2 | 1 | 2 | 4 |
| F7:T3 | 1 | 2 | 4 | b. Killing Rates

Table 8 shows the results of time-kill studies of 9:1, 8:2, and 7:3 fosfomycin:aminoglycoside combinations against *P. aeruginosa* ATCC 27853. Examination of bacterial killing over time revealed synergy between fosfomycin:tobramycin, fosfomycin: gentamicin, and fosfomycin:arbekacin combinations. The remaining fosfomycin:aminoglycoside combinations were not synergistic. This data shows that it was not obvious which combination of fosfomycin:aminoglycoside, nor which ratio of fosfomycin:amino glycoside would be synergistic.

TABLE 8

Time-kill studies with 9:1, 8:2, and 7:3 fosfomycin:aminoglycoside combinations against P. aeruginosa ATCC 27853. Antibiotics were evaluated at a concentration of 32 µg/mL.

| Antibiotic Combination | Synergy | | |
|---|---|---|---|
| | F9:A1 | F8:A2 | F7:A3 |
| Fosfomycin:Tobramycin | Yes | No | No |
| Fosfomycin:Gentamicin | Yes | No | No |
| Fosfomycin:Amikacin | No | No | No |
| Fosfomycin:Netilimicin | No | No | No |
| Fosfomycin:Arbekacin | No | No | Yes |
| Fosfomycin:Streptomycin | No | No | No |
| Fosfomycin:Neomycin | No | No | No |
| Fosfomycin:Kanamycin B | No | No | No |
| Fosfomycin:Dibekacin | No | No | No |

"F" = Fosfomycin and "A" = aminoglycoside

Table 9 shows the time to achieve bactericidal killing of P. aeruginosa ATCC 27853 by various fosfomycin:aminoglycoside combinations. Antibiotics were evaluated at a concentration of 32 µg/mL. This study demonstrated that the 9:1, 8:2, and 7:3 fosfomycin:tobramycin combinations achieved bactericidal killing faster than any other fosfomycin:aminoglycoside combination. The data also showed that three of the fosfomycin:aminoglycoside combinations did not exhibit bactericidal killing. These results were unexpected because tobramycin alone reached bactericidal killing at 1 hour, and fosfomycin alone was not bactericidal.

TABLE 9

Time to reach bactericidal killing of P. aeruginosa ATCC 27853 by 9:1, 8:2, and 7:3 fosfomycin:aminoglycoside combinations.

| Antibiotic Combination | Time (h) | | |
|---|---|---|---|
| | F9:A1 | F8:A2 | F7:A3 |
| Fosfomycin:Tobramycin | 2 | 1 | 1 |
| Fosfomycin:Gentamicin | 6 | 4 | 2 |
| Fosfomycin:Amikacin | 4 | 4 | 2 |
| Fosfomycin:Netilimicin | NC | NC | 6 |
| Fosfomycin:Arbekacin | NC | 4 | 2 |
| Fosfomycin:Streptomycin | NC | NC | NC |
| Fosfomycin:Neomycin | NC | NC | NC |
| Fosfomycin:Dibekacin | NC | 4 | 4 |

"NC" refers to not cidal
"F" = Fosfomycin and "A" = aminoglycoside

Figure 2:
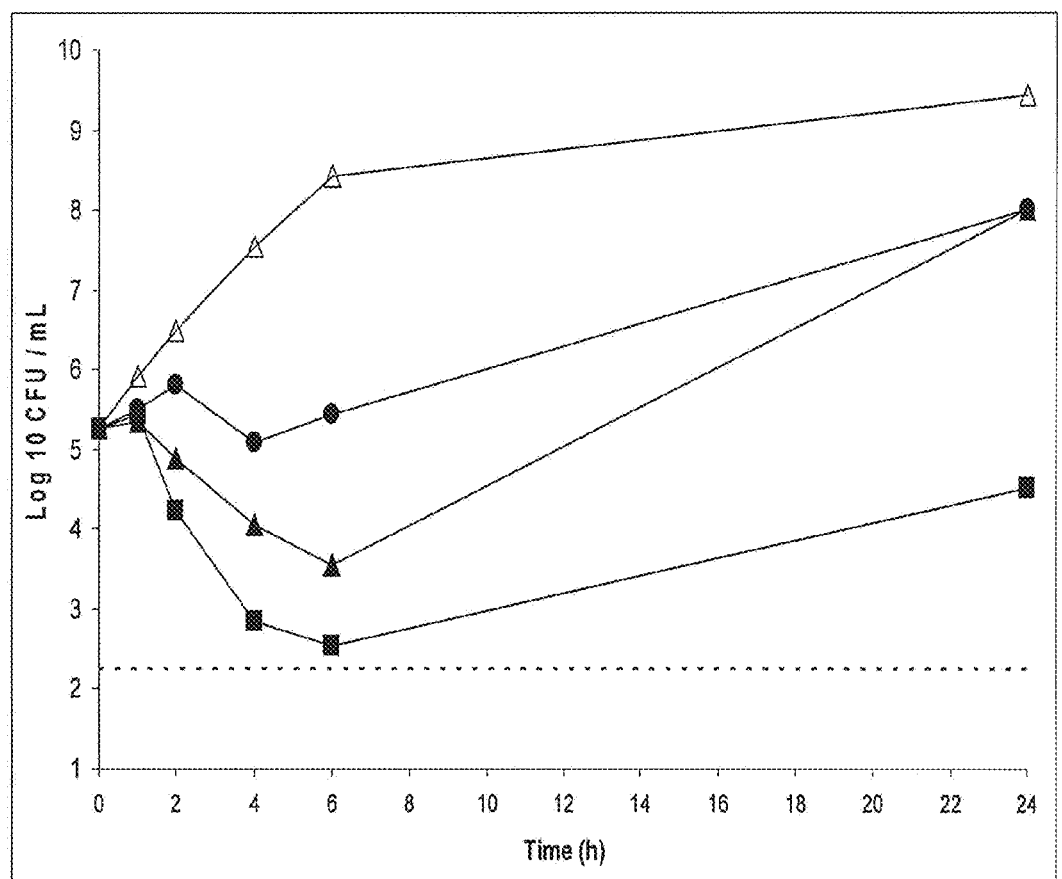

FIGS. 1 and 2 show time-kill curves for a 9:1 fosfomycin:tobramycin combination and demonstrate rapid bactericidal killing of P. aeruginosa ATCC 27853 compared to bacteriostatic killing of fosfomycin and tobramycin alone. This was unexpected since checkerboard analysis did not demonstrate synergy between fosfomycin and tobramycin.

Figure 3:
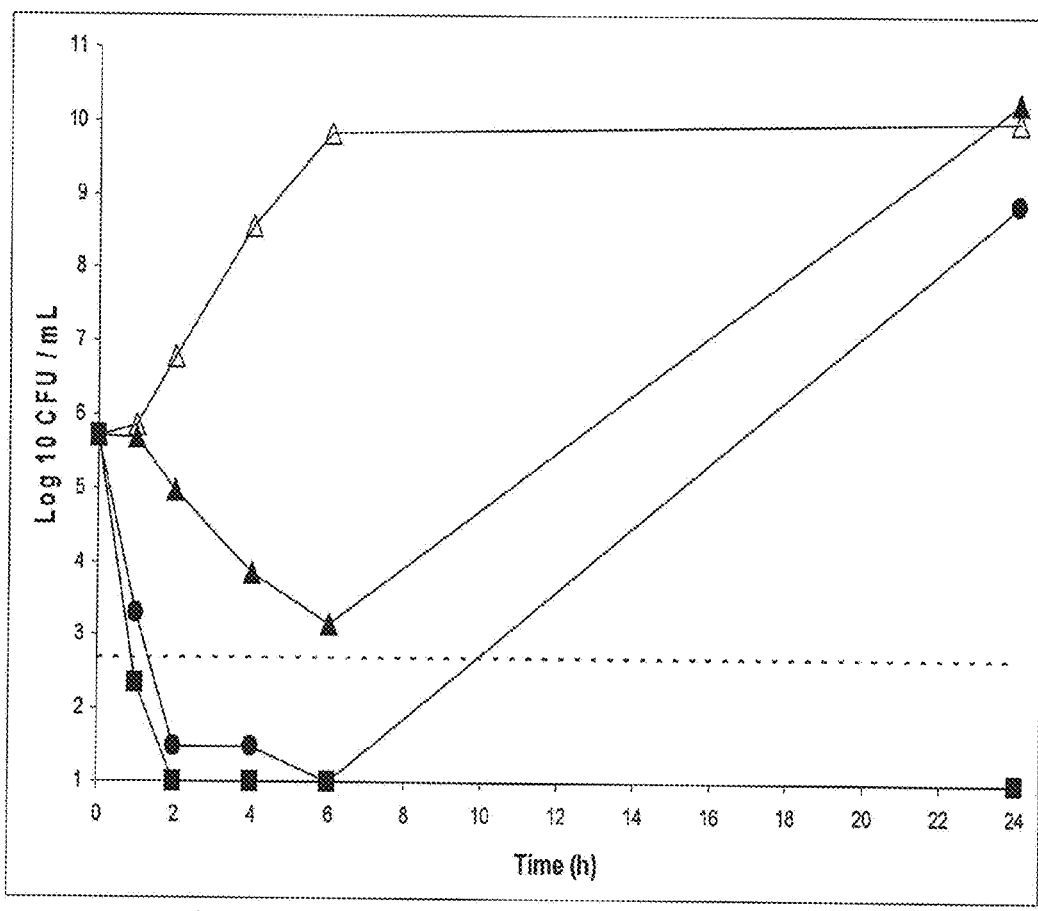
FIGS. 3 and 4 show time-kill curves for 8:2 fosfomycin:tobramycin combinations and demonstrate rapid bactericidal killing of *P. aeruginosa* ATCC 27853.
Figure 4:
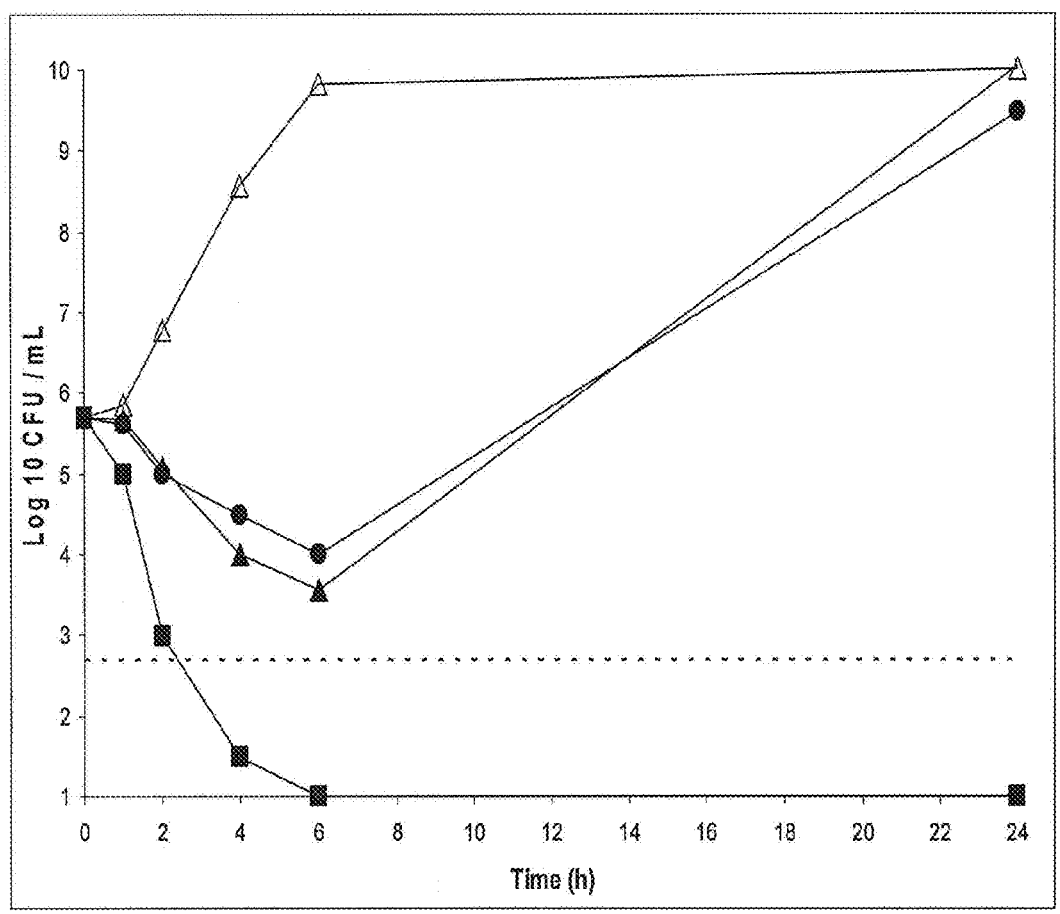

FIGS. 3 and 4 show time-kill curves for 8:2 fosfomycin:tobramycin combinations and demonstrate rapid bactericidal killing of P. aeruginosa ATCC 27853. At a concentration of 32 µg/mL, the killing activity of the combination was significantly superior to fosfomycin and slightly superior to tobramycin. At 16 µg/mL, the combination was superior to tobramycin and fosfomycin alone.

Figure 5:
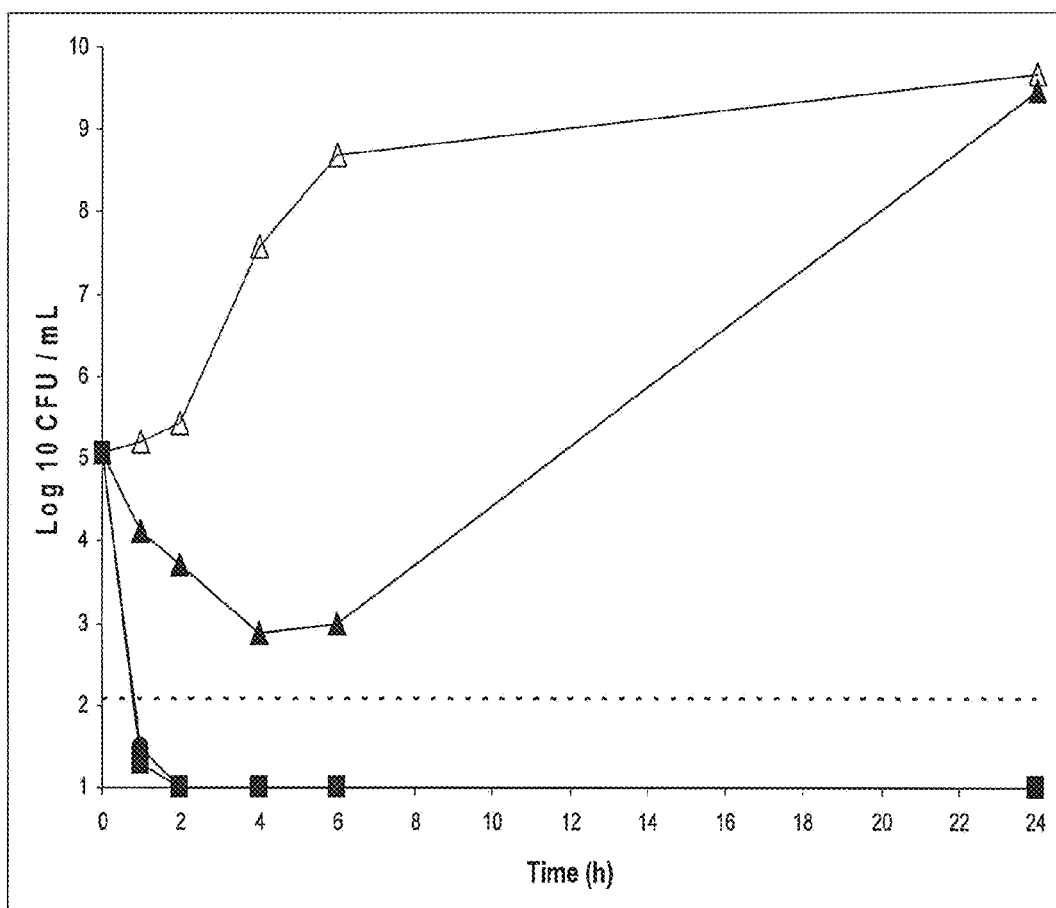
FIGS. 5, 6 and 7 show time-kill curves for 7:3 fosfomycin:tobramycin combinations and demonstrate rapid bactericidal killing of *P. aeruginosa* ATCC 27853.
Figure 6:
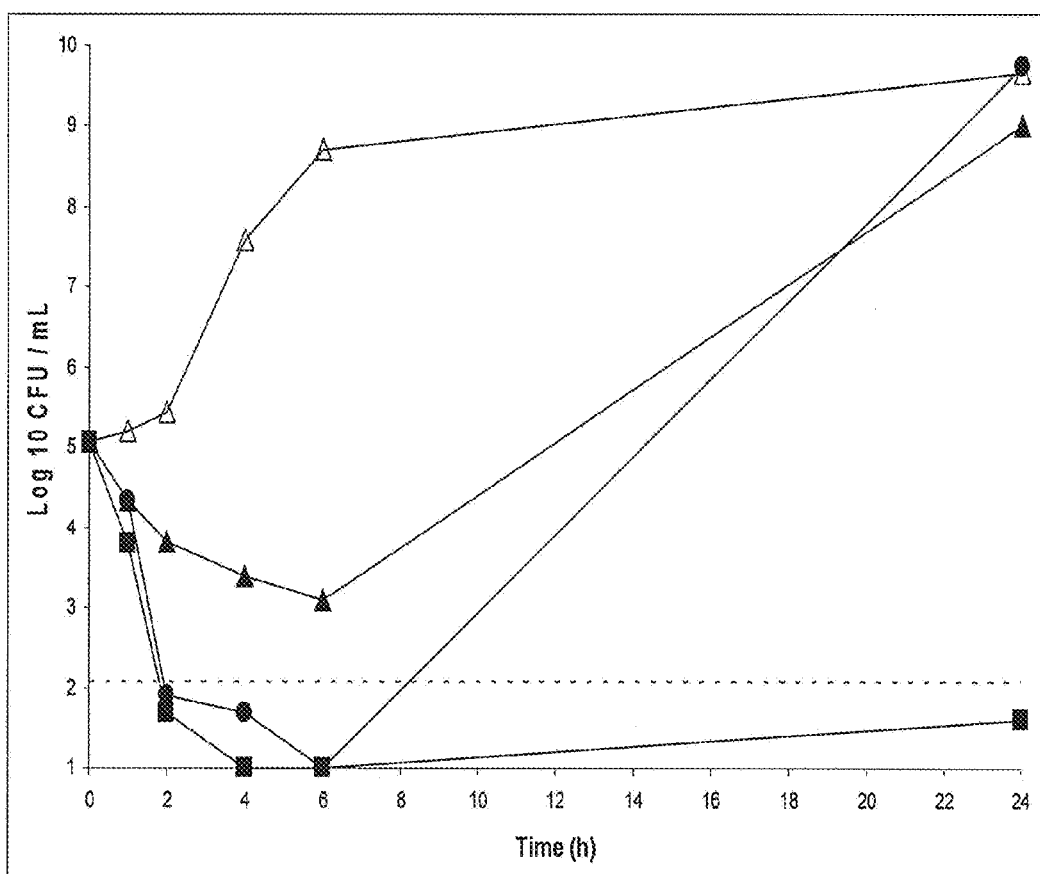
Figure 7:
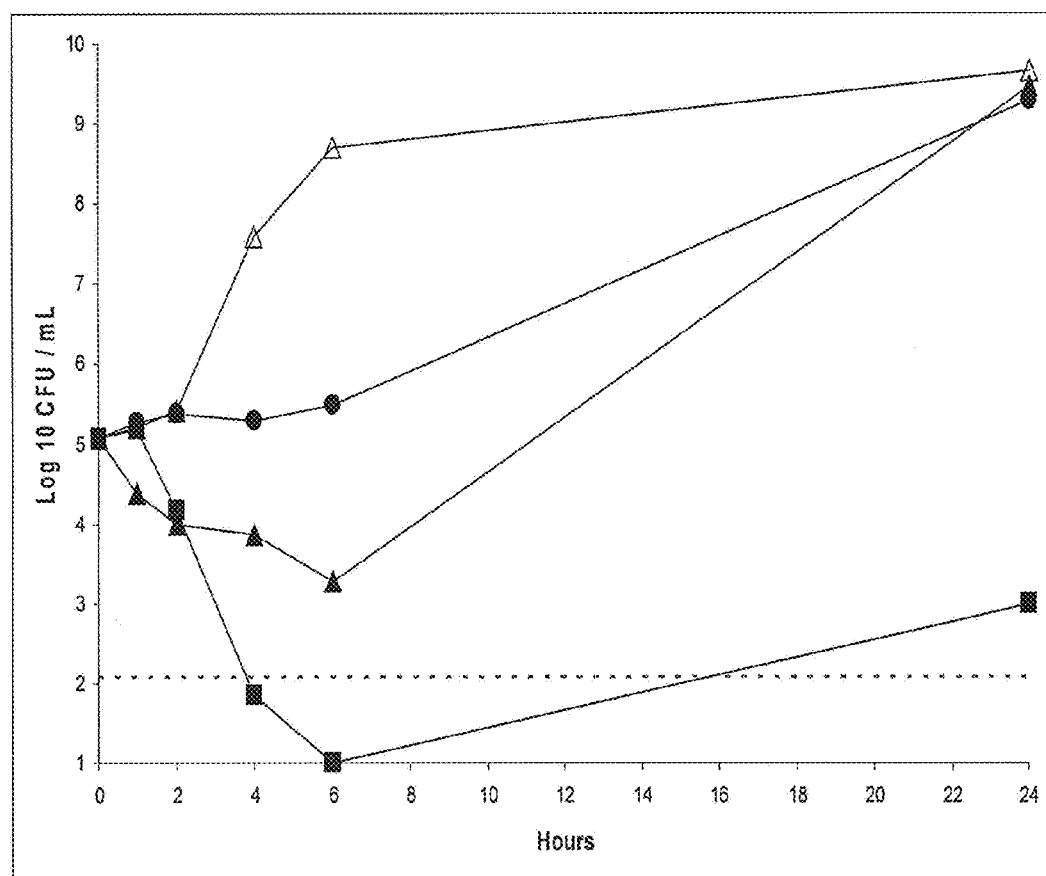

FIGS. 5, 6 and 7 show time-kill curves for 7:3 fosfomycin:tobramycin combinations and demonstrate rapid bactericidal killing of P. aeruginosa ATCC 27853. At concentrations of 16 µg/mL and 32 µg/mL, the killing activity of the combination was significantly superior to fosfomycin and slightly superior than tobramycin alone. At 8 µg/mL, the combination was superior to both tobramycin and fosfomycin alone.

Figure 8:
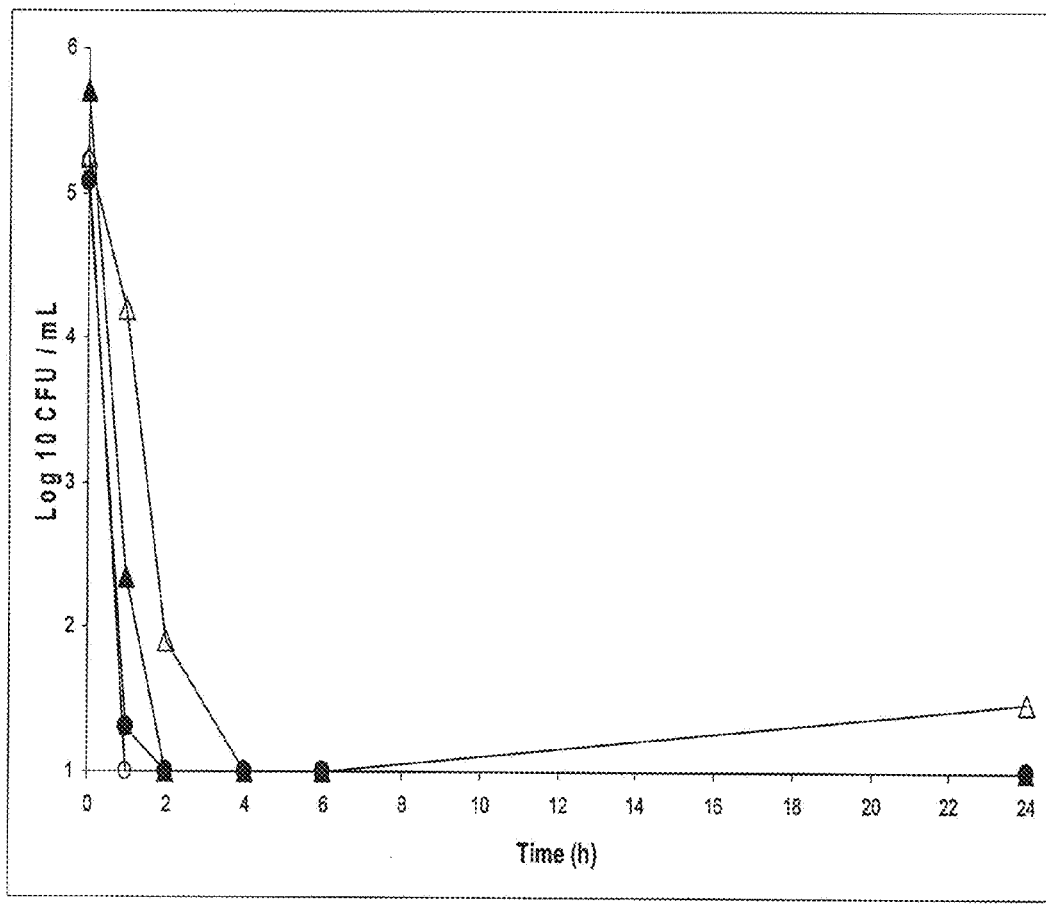
FIGS. 8 and 9 compare kill curves for 9:1, 8:2, and 7:3 fosfomycin:tobramycin combinations and tobramycin alone against *P. aeruginosa* ATCC 27853.
Figure 9:
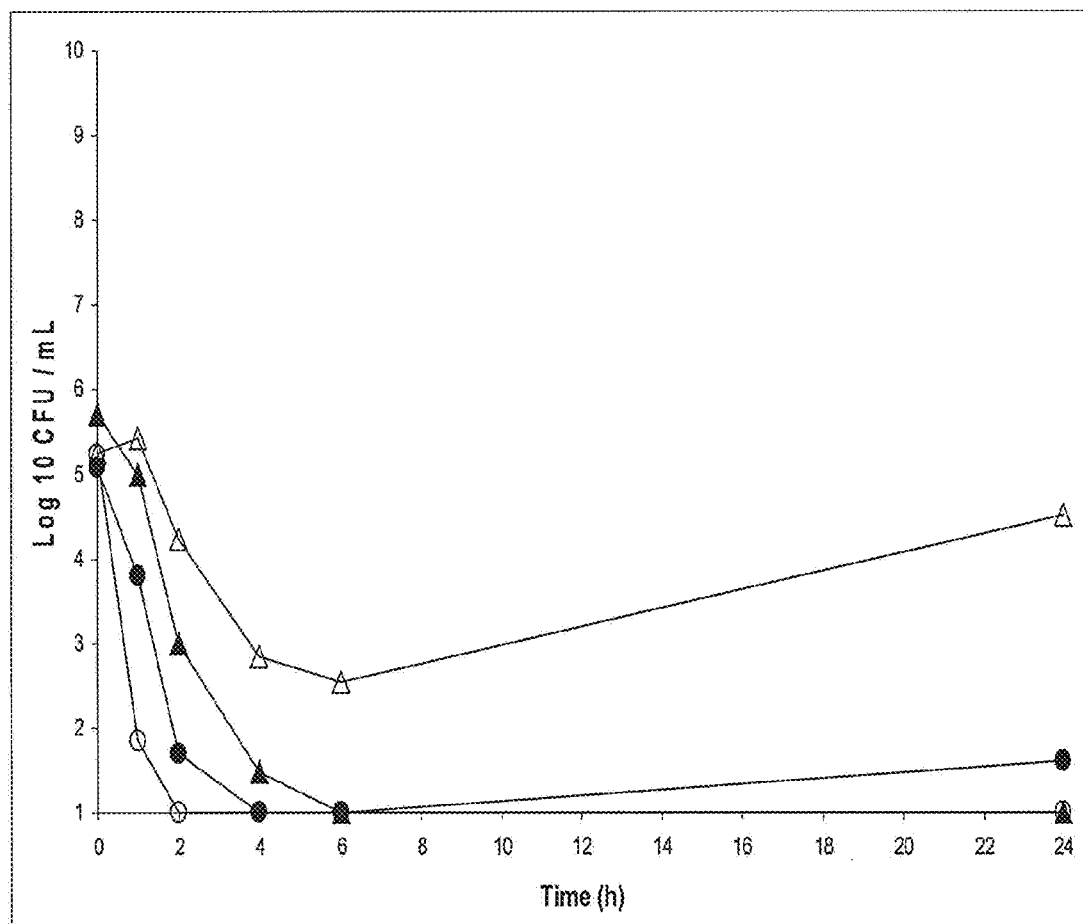

FIGS. 8 and 9 compare kill curves for 9:1, 8:2, and 7:3 fosfomycin:tobramycin combinations and tobramycin alone against P. aeruginosa ATCC 27853. At a concentration of 32 ug/mL, all the antibiotics had comparable rates and degrees of killing. At 16 ug/mL, tobramycin was the most active antibiotic followed by F7:A3, F8:A2, and F9:A1.

Figure 10:
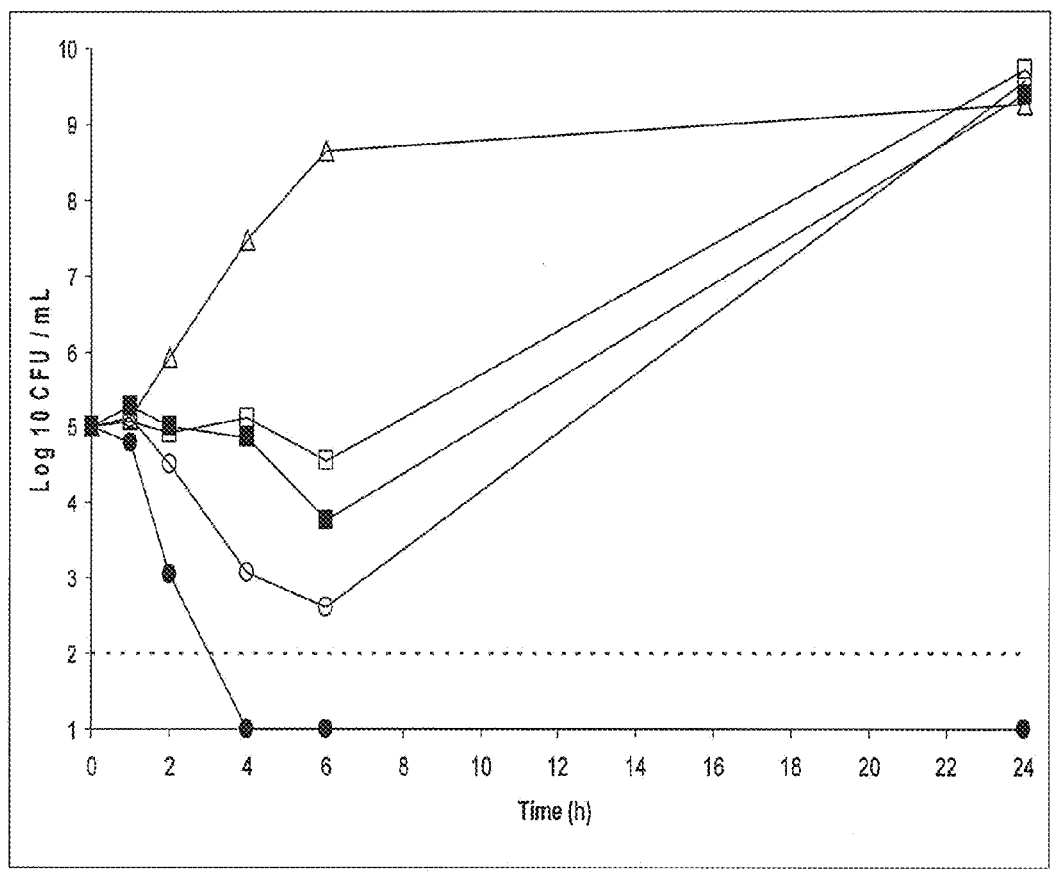
FIGS. 10, 11 and 12 demonstrate concentration-dependent killing of 9:1, 8:2, and 7:3 fosfomycin:tobramycin combinations against *P. aeruginosa* ATCC 27853.
Figure 11:
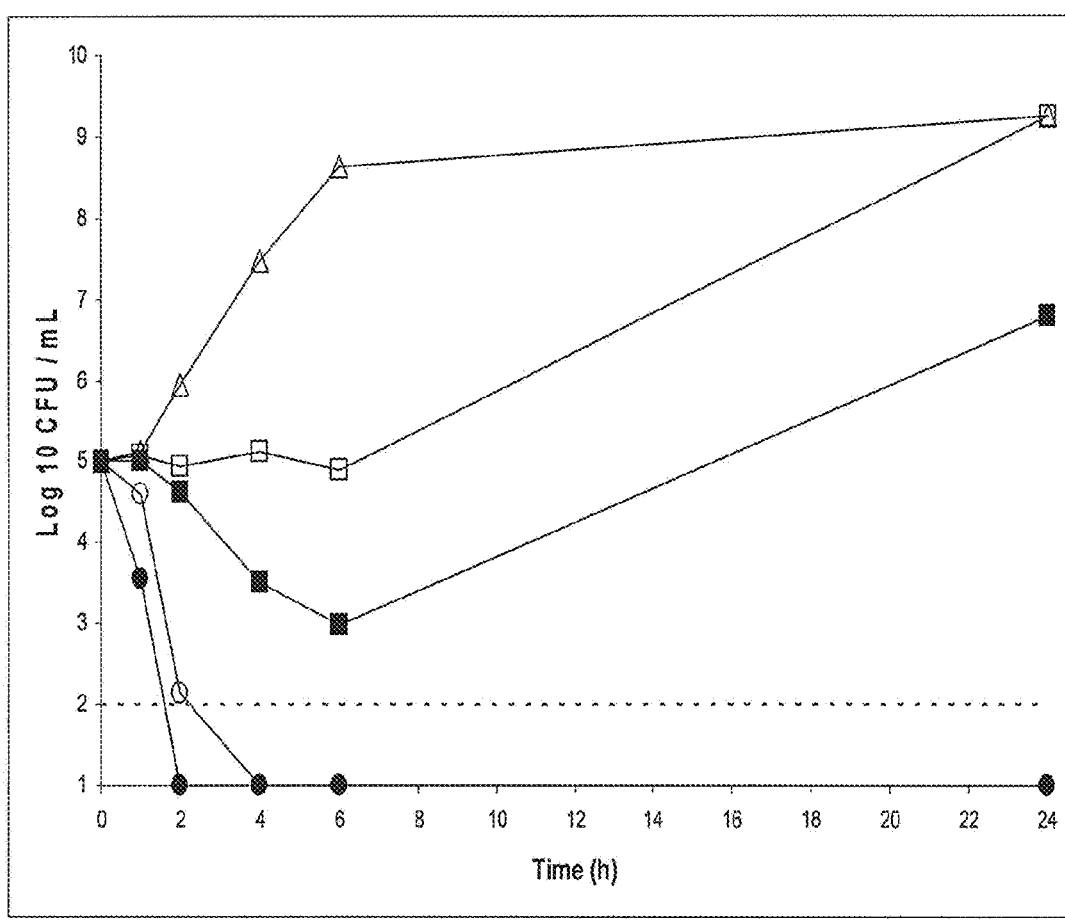
Figure 12:
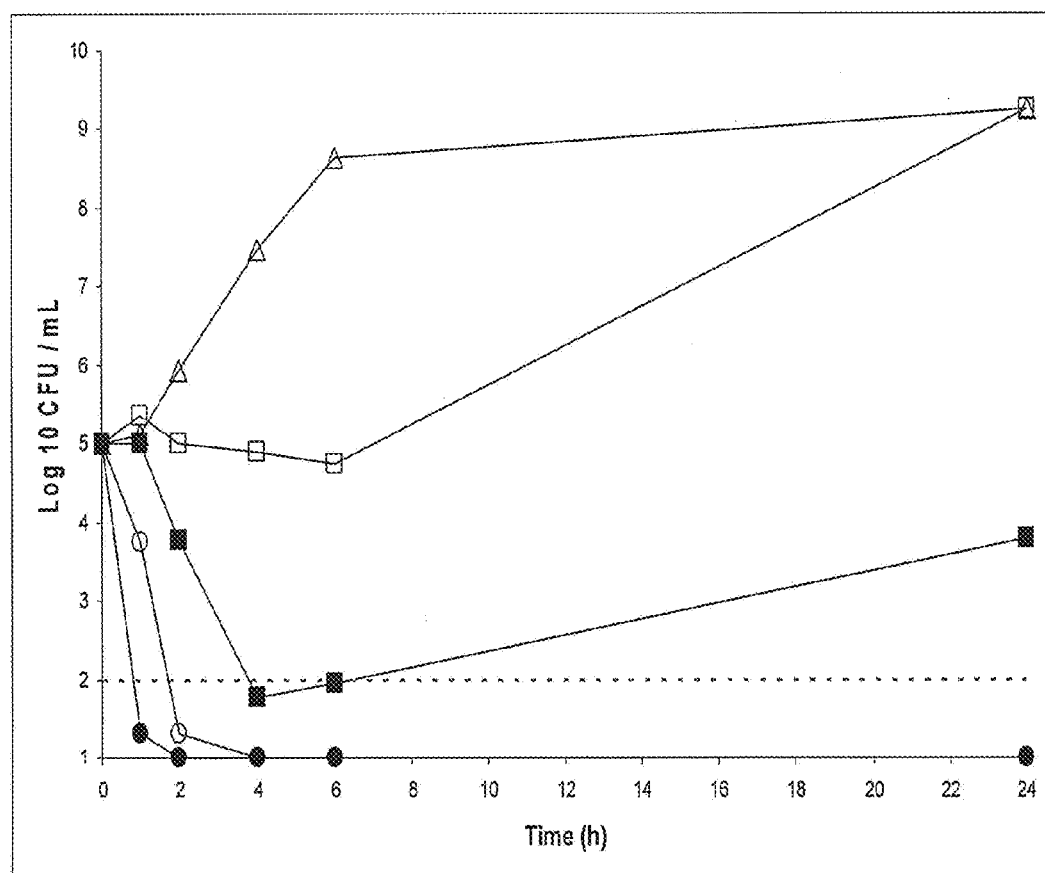

FIGS. 10, 11 and 12 demonstrate concentration-dependent killing of 9:1, 8:2, and 7:3 fosfomycin:tobramycin combinations against P. aeruginosa ATCC 27853. This was unexpected because the major component of the combination, fosfomycin, exhibits time-dependent killing. Tobramycin alone exhibits concentration-dependent killing.

c. Frequency of Resistance

Table 10 shows the frequency of development of resistance to fosfomycin and tobramycin alone, and a 9:1 fosfomycin:tobramycin combination for five P. aeruginosa strains. This study demonstrated the frequency of development of resistance to the 9:1 fosfomycin:tobramycin combination was 1000-100,000 times less than fosfomycin alone and 10-1000 times less than tobramycin alone.

TABLE 10

Frequency of development of resistance to fosfomycin, tobramycin and a 9:1 fosfomycin:tobramycin combination.

| P. aeruginosa Strains | Frequency of Resistance | | |
|---|---|---|---|
| | Fosfomycin | Tobramycin | Fos + Tob |
| COR-002 | $1.4 \times 10^{-3}$ | $6.7 \times 10^{-6}$ | $<2.9 \times 10^{-8}$ |
| COR-003 | $5.5 \times 10^{-4}$ | $3.2 \times 10^{-6}$ | $<1.2 \times 10^{-9}$ |
| COR-013 | $6.4 \times 10^{-3}$ | $2.6 \times 10^{-6}$ | $2.0 \times 10^{-7}$ |
| COR-014 | $1.5 \times 10^{-5}$ | $5.0 \times 10^{-6}$ | $<1.4 \times 10^{-9}$ |
| ATCC 27853 | $4.1 \times 10^{-5}$ | $3.4 \times 10^{-6}$ | $<2.5 \times 10^{-9}$ |

Table 11 shows the fold increase in the MIC of P. aeruginosa mutants isolated after a single exposure to fosfomycin, tobramycin, or a 9:1 combination of fosfomycin:tobramycin. This study demonstrated that the 9:1 mutants did not have a significant increase in MIC (1-2 fold), compared to fosfomycin (128→512 fold) or tobramycin (2-16 fold) mutants.

TABLE 11

Fold increase in MIC after a single exposure to antibiotic.

| P. aeruginosa Strain | Fold Increase in MIC | | |
|---|---|---|---|
| | F9:T1 | Fos | Tob |
| COR-002 | 1 | >256 | 1 |
| COR-003 | 2 | >256 | 2 |
| COR-013 | 1 | >64 | 8 |
| COR-014 | 1 | >512 | 16 |
| ATCC 27853 | 2 | 128 | 1 |

Table 12 shows the development of resistance in a clinical P. aeruginosa strain after 28 days of continuous exposure to fosfomycin, tobramycin or a 9:1 fosfomycin:tobramycin combination. Exposure to the 9:1 combination caused a 8-fold increase in MIC by day 14, but the MIC did not exceed the fosfomycin resistance breakpoint of 256 µg/mL. Exposure to tobramycin increased the MIC 128-fold which exceeded the tobramycin resistance breakpoint of 16 µg/mL. A rapid and dramatic development of resistance was observed with P. aeruginosa exposed to fosfomycin alone.

TABLE 12

Development of resistance after continuous exposure to antibiotic.

| Antibiotic | MIC (μg/mL) | | | | |
|---|---|---|---|---|---|
| | 0d | 7d | 14d | 21d | 28d |
| F9:T1 | 8 | 16 | 64 | 64 | 64 |
| Tobramycin | 0.5 | 0.5 | 0.5 | 32 | 64 |
| Fosfomycin | 16 | >512 | >512 | >512 | >512 | d. Animal Efficacy

Figure 13:
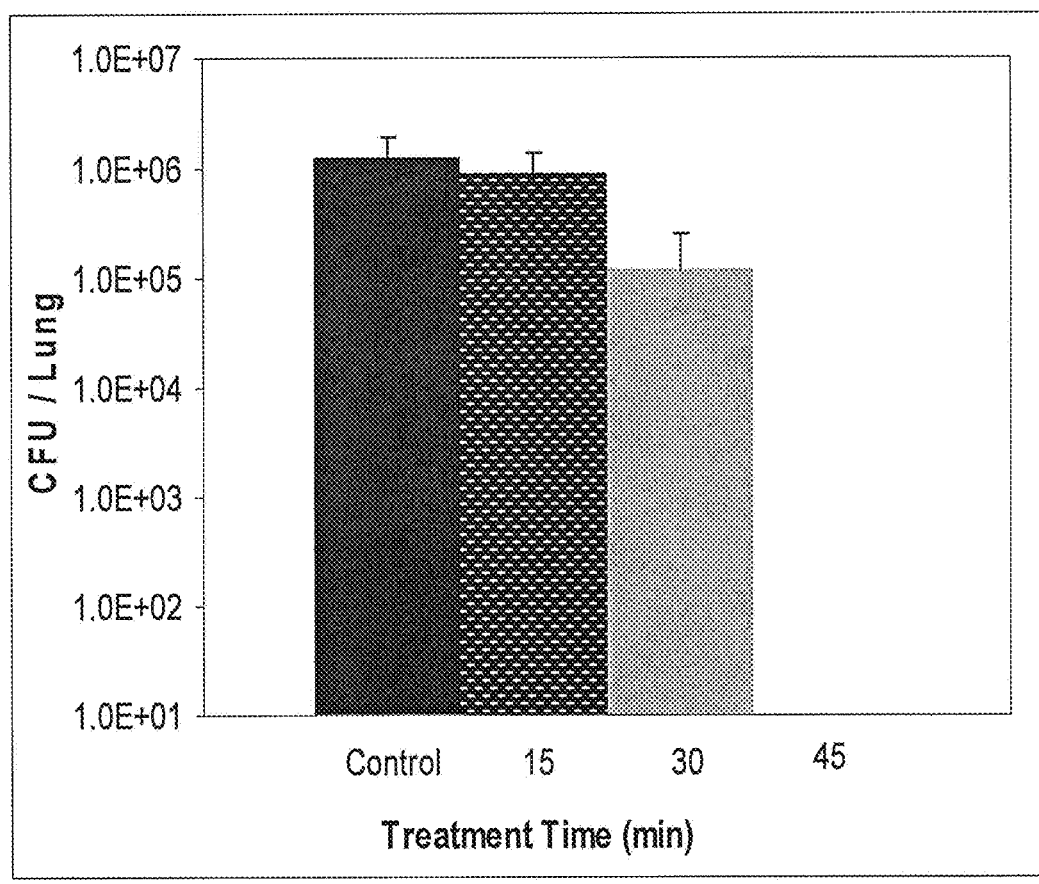
FIGS. 13, 14, and 15 show the killing of *E. coli* in the rat lung after aerosol administration of a 31.1 mg/mL solution of a 9:1, 8:2, and 7:3 fosfomycin:tobramycin combinations, respectively.
Figure 14:
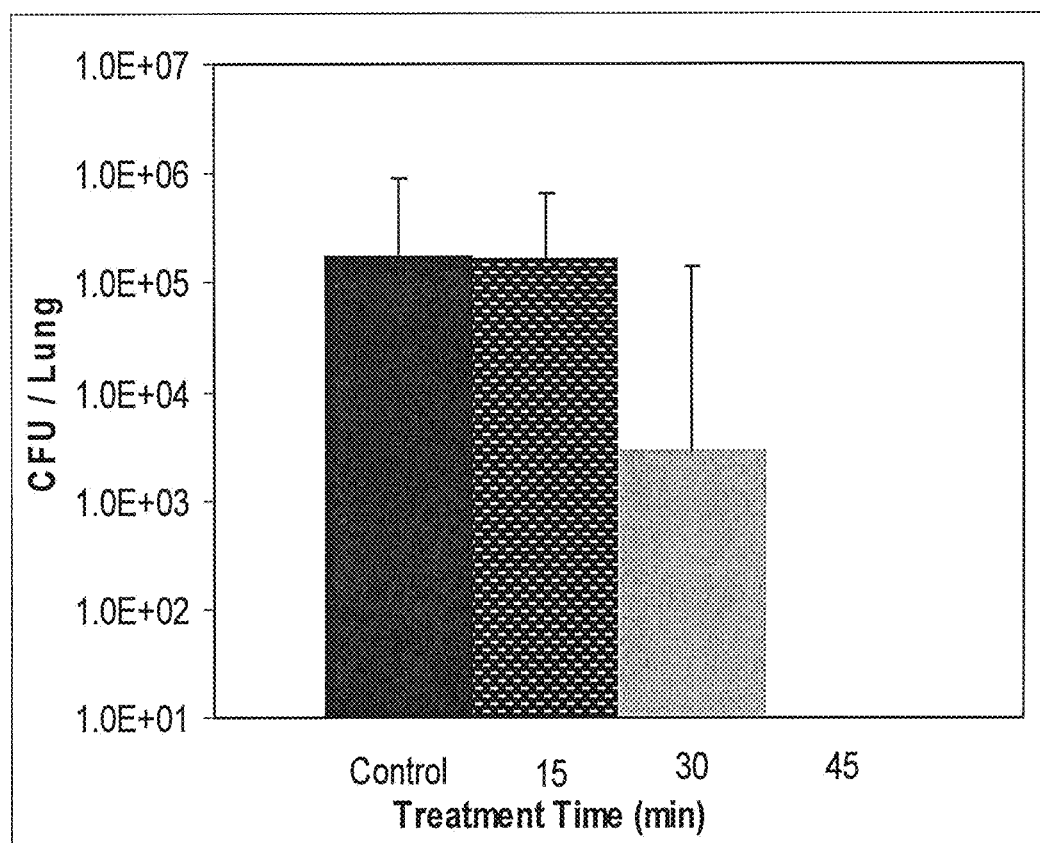
Figure 15:
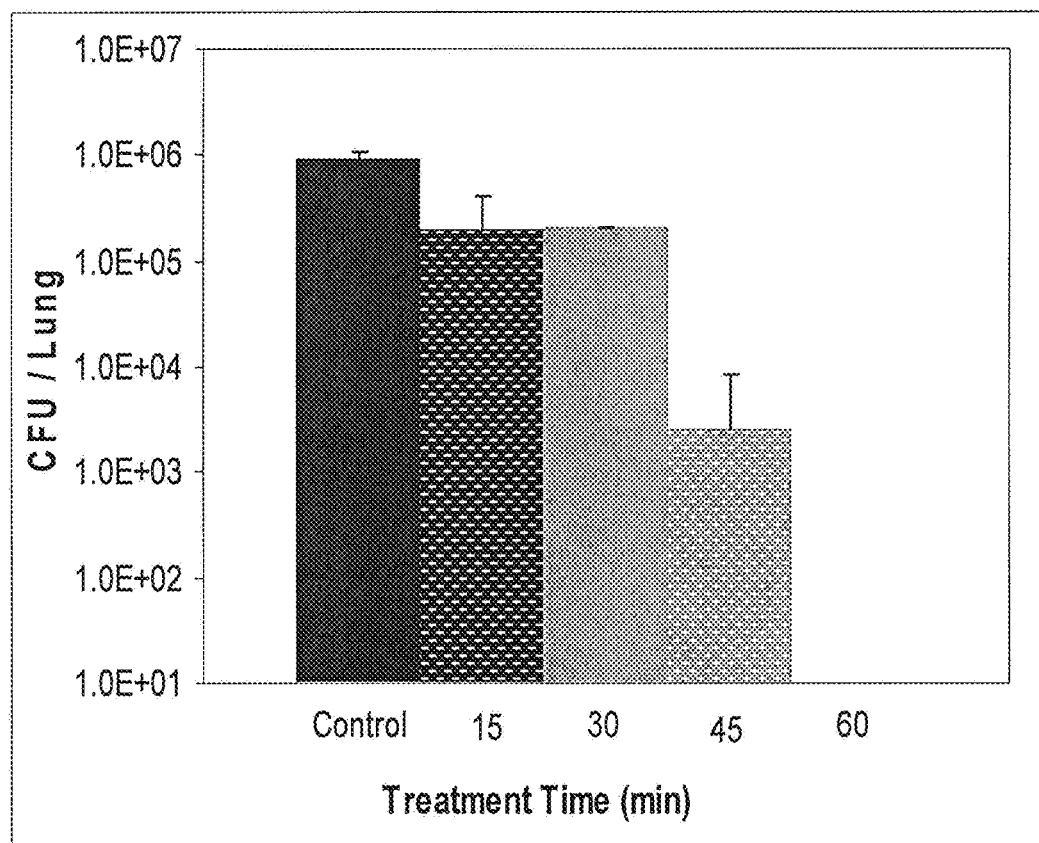

FIGS. 13, 14, and 15 show the killing of *E. coli* in the rat lung after aerosol administration of a 31.1 mg/mL solution of a 9:1, 8:2, and 7:3 fosfomycin:tobramycin combinations, respectively. This study demonstrated complete eradication (5-6 Log 10 CFU) of the *E. coli* lung infection after 45-60 minutes of treatment.

Figure 16:
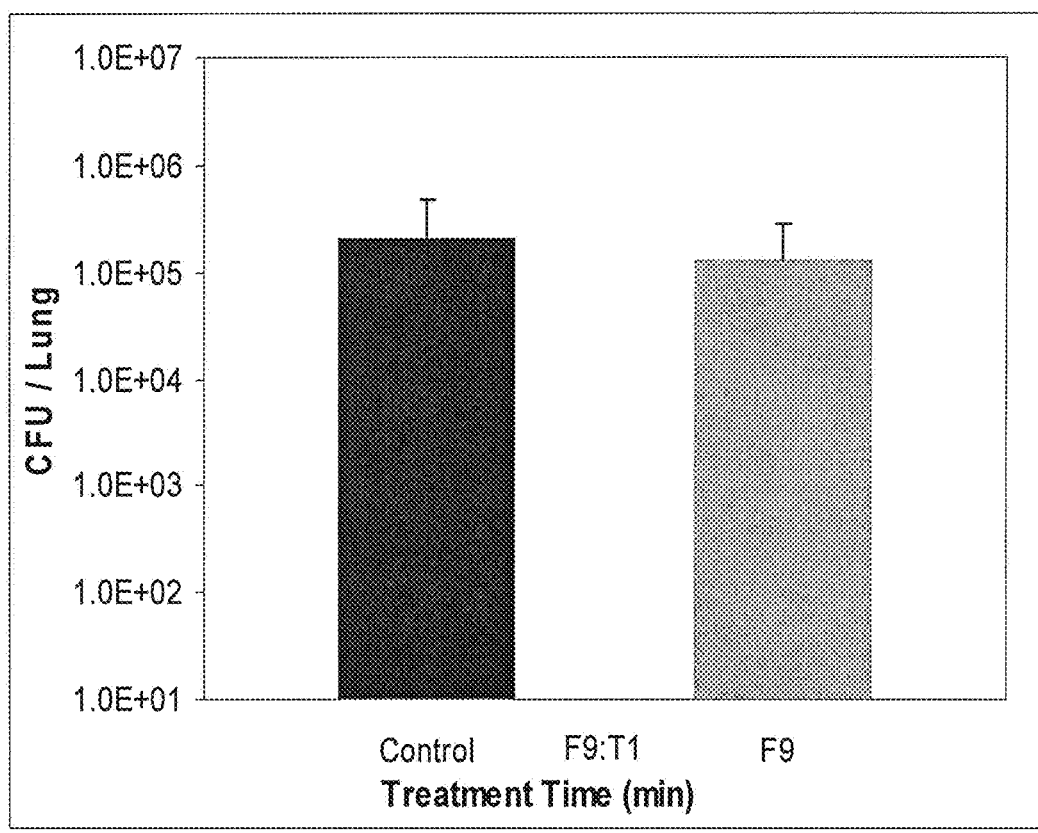
FIGS. 16 and 17 demonstrate that aerosol administration of a 31.1 mg/mL solution of a 9:1 fosfomycin:tobramycin combination resulted in >5 log 10 killing of *E. coli* in the rat lung, compared to less than 1 log 10 killing fosfomycin and tobramycin alone.
Figure 17:
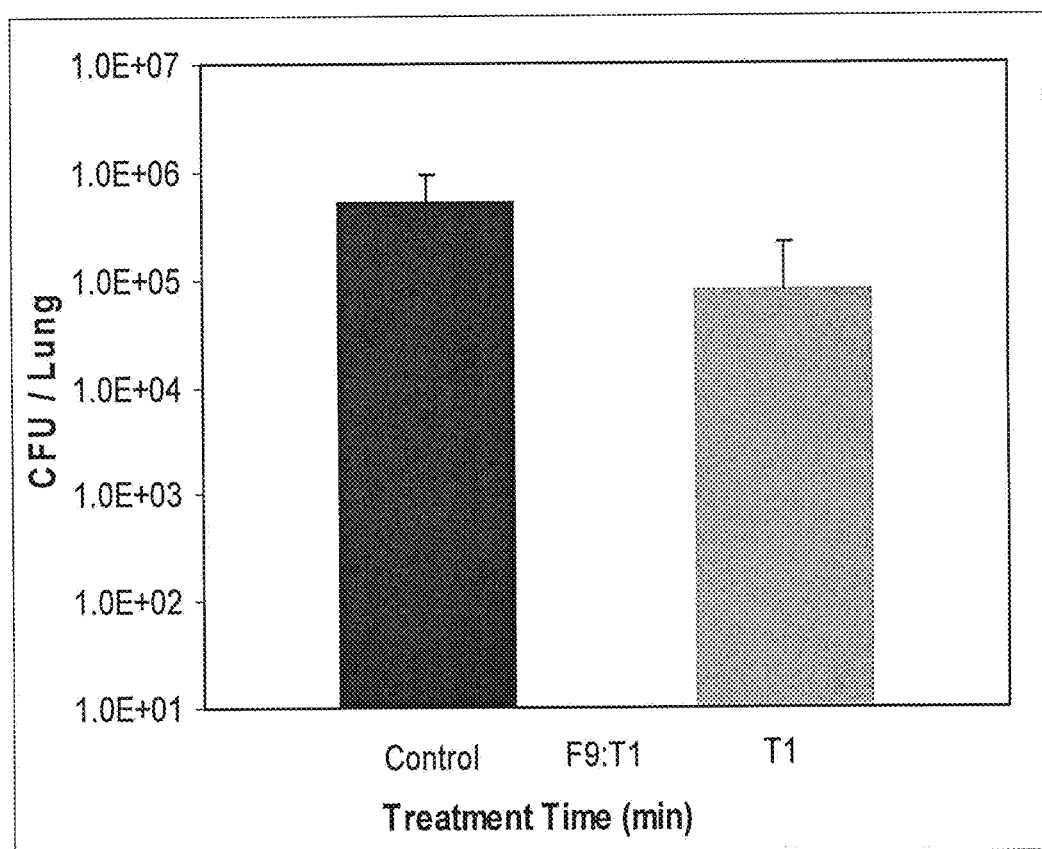
Figure 18:
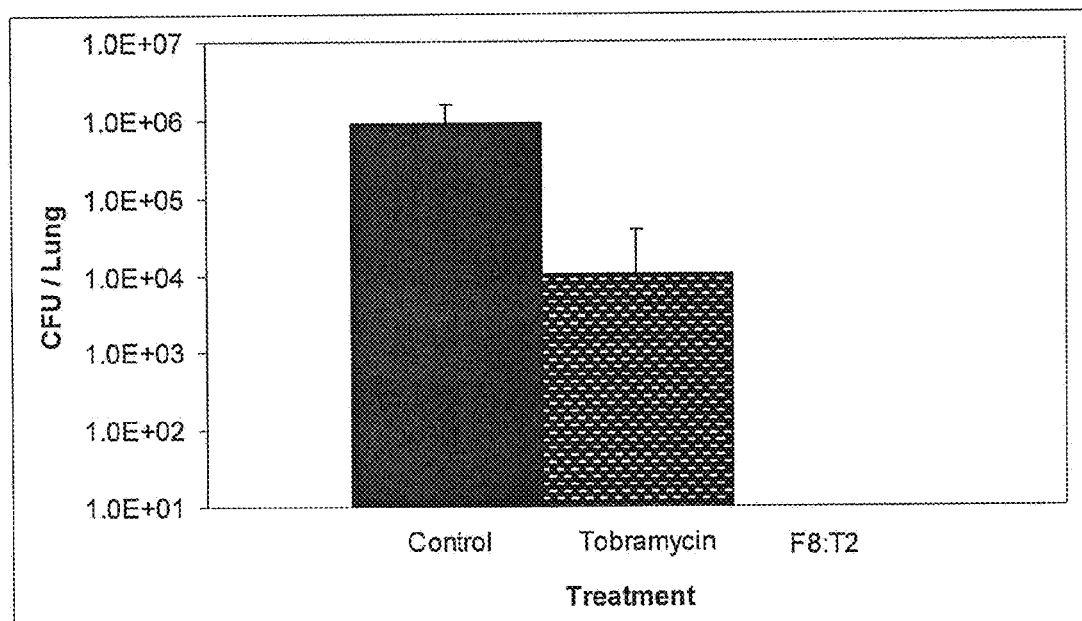
FIG. 18 demonstrates that aerosol administration of a 31.1 mg/mL solution of a 8:2 fosfomycin:tobramycin combination resulted in >5 log 10 killing of *E. coli* in the rat lung, compared to 2 log 10 killing by aerosol administration of a 40 mg/mL solution of tobramycin alone.

FIGS. 16 and 17 demonstrate that aerosol administration of a 31.1 mg/mL solution of a 9:1 fosfomycin:tobramycin combination resulted in >5 log 10 killing of *E. coli* in the rat lung, compared to less than 1 log 10 killing fosfomycin and tobramycin alone.

Figure 20:
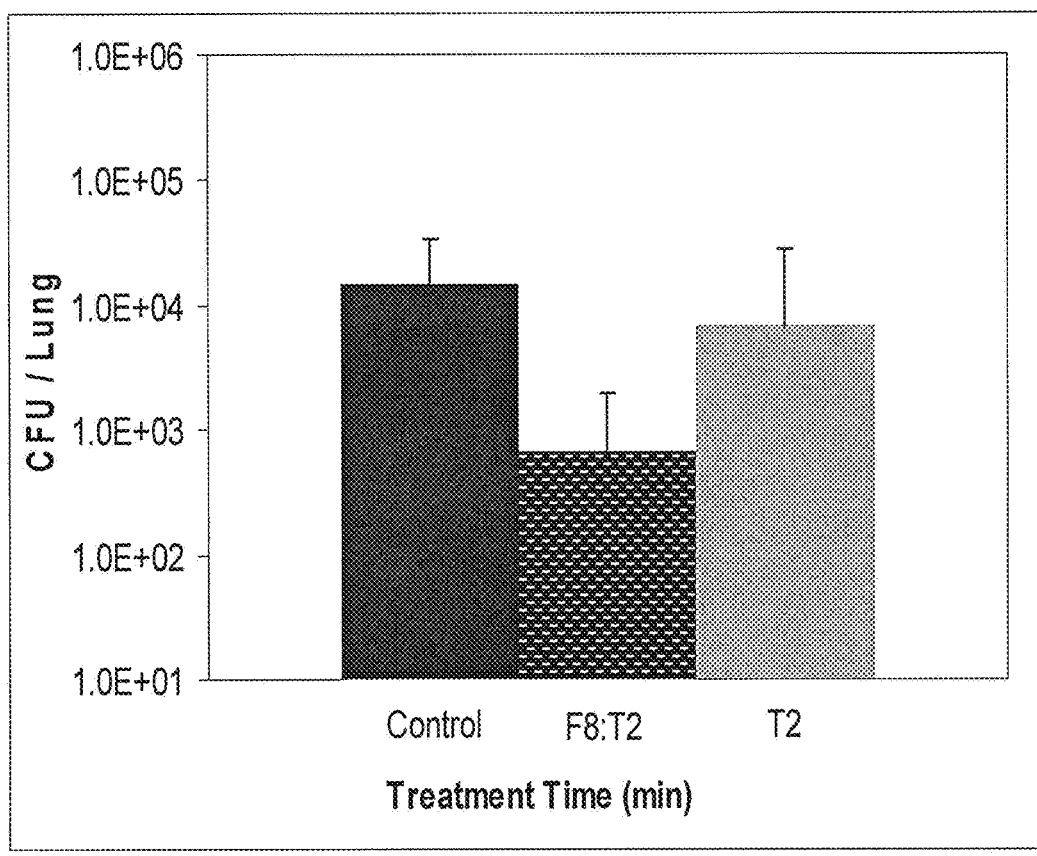

FIG. 20 demonstrates that aerosol administration of a 31.1 mg/mL solution of a 8:2 fosfomycin:tobramycin combination resulted in >5 log 10 killing of *E. coli* in the rat lung, compared to 2 log 10 killing by tobramycin alone. This was unexpected because the in vitro potency data did not demonstrate that the combination was superior to tobramycin alone.

Figure 19:
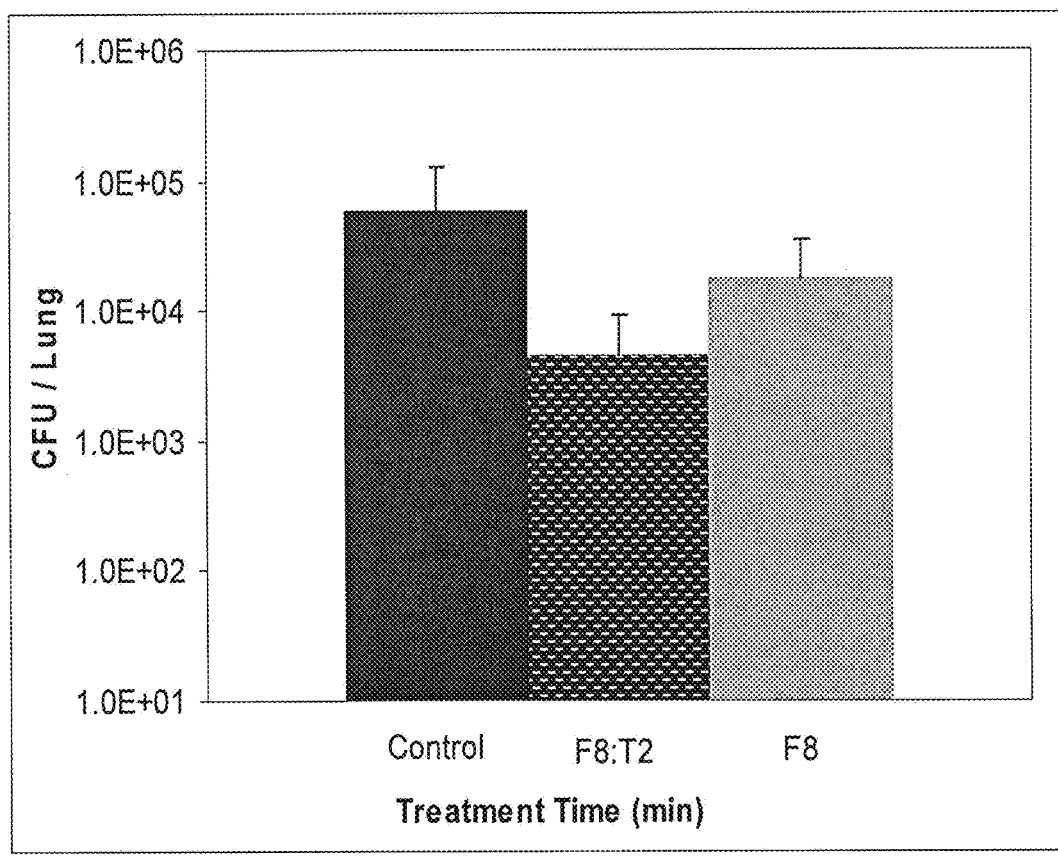
FIGS. 19 and 20 demonstrate that aerosol administration of a 31.1 mg/mL solution of a 8:2 fosfomycin:tobramycin combination resulted in greater killing of *P. aeruginosa* in the rat lung, compared to fosfomycin and tobramycin alone.

FIGS. 19 and 20 demonstrate that aerosol administration of a 31.1 mg/mL solution of a 8:2 fosfomycin:tobramycin combination resulted in greater killing of *P. aeruginosa* in the rat lung, compared to fosfomycin and tobramycin alone.

Figure 21:
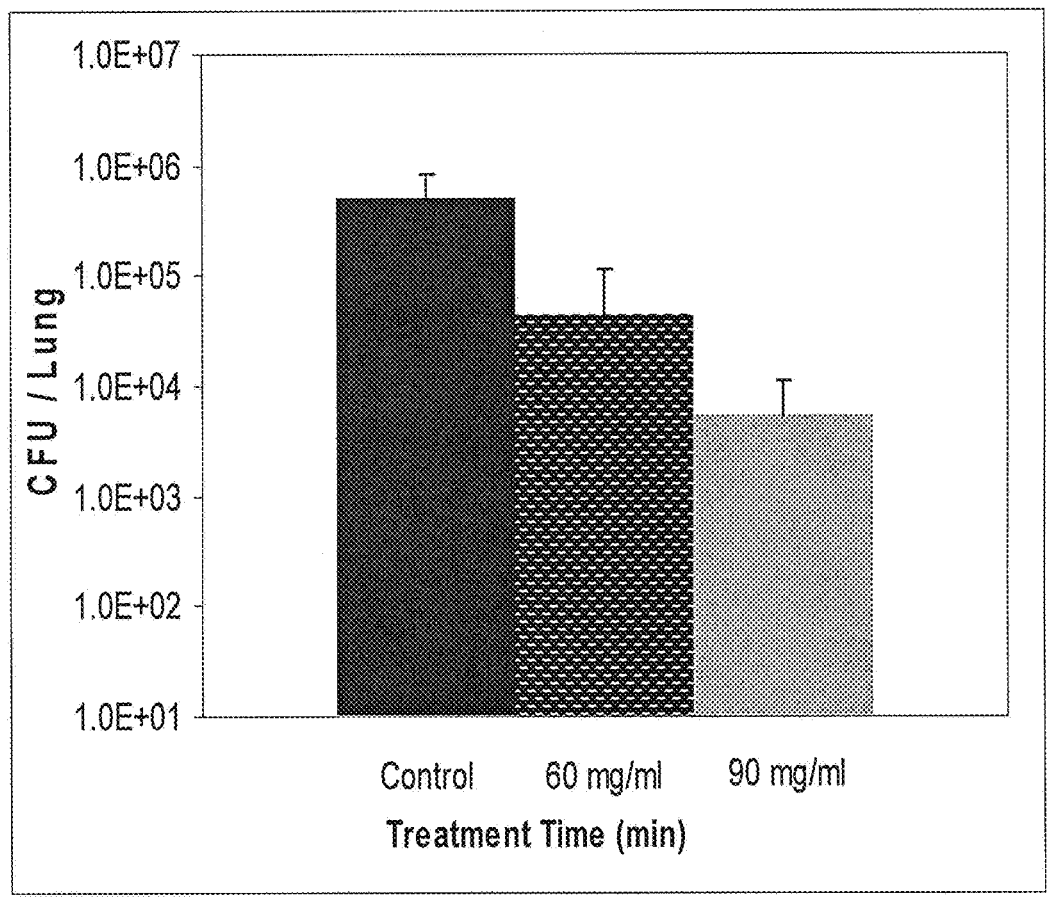
FIG. 21 demonstrates that aerosol administration of a 60 and 90 mg/mL solution of a 8:2 fosfomycin:tobramycin combination resulted in significant killing of *P. aeruginosa* in the rat lung.

FIG. 21 demonstrates that aerosol administration of a 60 and 90 mg/mL solution of a 8:2 fosfomycin:tobramycin combination resulted in significant killing of *P. aeruginosa* in the rat lung.

II. Aerosol Fosfomycin/Tobramycin Formulation

Aminoglycosides useful in the invention are antibiotics, such as tobramycin, gentamicin, kanamycin B, amikacin, arbekacin, dibekacin, streptomycin, neomycin, and netilmicin. Fosfomycin compounds particularly useful in the invention are antibiotics, such as fosfomycin trometamol, fosfomycin disodium salt, and fosfomycin calcium.

The preferred fosfomycin plus tobramycin formulation according to the invention contains 10-500 mg of fosfomycin plus tobramycin per 0.5-7 mL of water with a chloride concentration >30 mM. This corresponds to doses that would be required to prevent colonization or to treat severe upper and lower respiratory tract infections caused by a range of susceptible organisms.

Patients can be sensitive to the pH, osmolarity, and ionic content of a nebulized solution. Therefore these parameters should be adjusted to be compatible with fosfomycin plus tobramycin and tolerable to patients. The most preferred solution or suspension of fosfomycin plus tobramycin will contain a chloride concentration >30 mM at pH 4.5-8.0.

The formulation of the invention is nebulized predominantly into particle sizes allowing delivery of the drug into the terminal and respiratory bronchioles or nasal passages where the bacteria reside during infection and colonization. For efficacious delivery of fosfomycin plus tobramycin to the lung endobronchial space of airways in an aerosol, the formation of an aerosol having a mass median aerodynamic diameter predominantly between 1 to 5μ is necessary. The formulated and delivered amount of fosfomycin plus tobramycin for the treatment and prophylaxis of endobronchial infections, particularly those caused by the *P. aeruginosa* must effectively target the lung surface. The formulation must have the smallest possible aerosolizable volume able to deliver an effective dose of fosfomycin plus tobramycin to the site of the infection. The formulation must additionally provide conditions which would not adversely affect the functionality of the airways and nasal passages. Consequently, the formulation must contain enough of the drug formulated under the conditions to allow its efficacious delivery, while avoiding undesirable reactions. The new formulation according to the invention meets all these requirements.

According to the invention, fosfomycin plus tobramycin is formulated in a liquid dosage form intended for inhalation therapy by patients with, or at risk to acquire, bacterial upper or lower respiratory infection. Since the patients reside throughout the world, it is imperative that the liquid dosage formulation has reasonably long shelf-life. Storage conditions and packaging thus become important.

The formulation of fosfomycin plus tobramycin can be aseptically prepared as an aqueous solution in a dual blow-fill ampoule such that each antibiotic is independently formulated in water and pH adjusted. Tobramycin is formulated at acidic pH (1-6) while fosfomycin is formulated at basic pH (8-13). The low pH formulation for tobramycin assures that all of its basic nitrogen atoms are protonated thus protecting the molecule from amine oxidation and degradation (tobramycin solutions turn yellow at room temperature). Thus, the low pH solutions of tobramycin are stable at room temperature for indefinite periods of time. Fosfomycin is most stable at high pH as the reactive epoxide ring is prone to hydrolysis (ring opening) at acidic or low pH. High pH solutions of fosfomycin are also stable at room temperature. Therefore, the dual ampoule blow-fill container allows for the separate and room temperature stable formulation of each antibiotic at high and low pH such that the drug product combination and final pH is created by mixing both solutions in the nebulizer immediately before use. The storage suitability of the formulation allows reliable usage of the formulated fosfomycin plus tobramycin suitable for aerosolization.

III. Nebulizers for Pulmonary Delivery of the Antibiotic Combination

A device able to nebulize the formulation of the invention into aerosol particles predominantly in the 1 to 5μ size range is utilized to administer the formulations of the present invention. Predominantly in this application means that at least 70% but preferably more than 90% of all generated aerosol particles are within the 1 to 5μ range. Typical devices include jet nebulizers, ultrasonic nebulizers, pressurized aerosol generating nebulizers, and vibrating porous plate nebulizers. Representative suitable nebulizers include the eFlow® nebulizer available from Pari Inovative Manufactures, Midlothian, Va.; the iNeb® nebulizer available from Profile Drug Delivery of West Sussex, United Kingdom; the Omeron MicroAir® nebulizer available from Omeron, Inc. of Chicago, Ill. and the AeroNebGo® nebulizer available from Aerogen Inc. of Mountain View, Calif.

A jet nebulizer utilizes air pressure to break a liquid solution into aerosol droplets. An ultrasonic nebulizer works by a piezoelectric crystal that shears a liquid into small aerosol droplets. Pressurized systems general force solutions through small pores to generate small particles. A vibrating porous plate device utilizes rapid vibration to shear a stream of liquid into appropriate droplet sizes. However, only some formulations of fosfomycin plus tobramycin can be efficiently nebulized as the devices are sensitive to the physical and chemical properties of the formulation.

The invention is a small volume, high concentration formulation of fosfomycin plus tobramycin that can be delivered as an aerosol at efficacious concentrations of the drug to the respiratory tract in people at risk for, or suffering from infection caused by susceptible bacteria. The formulation is safe, well tolerated, and very cost effective. Furthermore, the formulation provides adequate shelf life for commercial distribution. The foregoing may be better understood from the following examples, which are presented for the purposes of illustration and are not intended to limit the scope of the inventive concepts.

EXAMPLE 1

Preparation of Fosfomycin/Tobramycin Solutions for Aerosolization

9:1 Fosfomycin/Tobramycin Solution

Fosfomycin disodium (18.057 g, 13.99 g free acid) was dissolved in 250 mL of water and the pH was adjusted to 7.41 by the dropwise addition of 1.53 mL of 4.5 N HCl. To the resulting solution was added 1.56 g of 97.5% tobramycin base. The pH of the solution was adjusted to 7.60 by the addition of 2.45 mL of 4.5 N HCl. The solution was diluted to 500 mL with water and filtered through a 0.2 μm Nalge Nunc 167-0020 membrane filter. The final pH was 7.76, the osmolality was 537 mOsmol/kg, the fosfomycin/tobramycin ratio was calculated to be 9:1, and the chloride concentration was 35.8 mM.

8:2 Fosfomycin/Tobramycin Solution

A solution of fosfomycin/tobramycin in a 8:2 ratio was prepared. 3.1680 g of fosfomycin disodium (2.4013 g free acid) was dissolved in 50 ml water. 0.6154 g of 97.5% tobramycin base (0.6000 g of pure tobramycin base) was dissolved in the fosfomycin solution. The pH adjusted by adding 0.910 mL of 6 M HCl. The solution was diluted to 100 mL with water. The final pH of the solution was 7.65, osmolality was 477 mOsmol/kg, and the chloride concentration was 54.6 mM. The final fosfomycin/tobramycin ratio was calculated to be 8:2

7:3 Fosfomycin/Tobramycin Solution

Using the procedure described for the 9:1 solution, above, a solution of fosfomycin/tobramycin in a 7:3 ratio was prepared; 17.466 g of fosfomycin disodium (13.239 g free acid) was dissolved in water; the pH adjusted to 7.43 by adding 1.46 mL of 4.5 N HCl, 5.819 g of 97.5% tobramycin base (5.674 g of pure tobramycin base), and the pH of the combined solution was adjusted by adding 9.20 mL of 4.5 N HCl. The final pH of the solution was 7.68, the osmolality was 560 mOsmol/kg, the fosfomycin/tobramycin ratio was 7:3, and the chloride concentration was 95.9 mM.

EXAMPLE 2

Preparation of A 8:2 Hyperosmolar Solution of Fosfomycin and Tobramycin 7.9165 g of fosfomycin disodium (6.0007 g of fosfomycin free acid) and 1.5382 g of 97.5% tobramycin base (1.4997 g of pure tobramycin base) were dissolved in 50 mL water. The pH was adjusted to 7.62 by the addition of 2.3 mL of 6 M HCl. The combined solution was diluted to 100 mL. The final pH was 7.64, the osmolality was 1215 mOsmol/kg, the final chloride concentration was 138 mM, and the fosfomycin/tobramycin ratio was 8:2.

EXAMPLE 3

Preparation of Individual Solutions of High pH Fosfomycin and Low pH Tobramycin for Reconstitution A fosfomycin solution was prepared by dissolving 5.891 g of fosfomycin disodium (4.465 g of fosfomycin free acid) in water and diluting to 100 mL. The pH was 9.42, and the osmolality was 795 mOsmol/kg.

A tobramycin solution was prepared by dissolving 1.869 g of 97.5% tobramycin base (1.822 g of pure tobramycin base) in 60 mL water, adjusting the pH to 4.90 by adding 18.8 mL of 1 M HCl, and diluting to 100 ml with water. The pH was 4.89, and the osmolality was 148 mOsmol/kg.

1 mL of the fosfomycin solution and 1 mL of the tobramycin solution were combined. For the combined drug product solution, the pH was 7.30, the osmolality was 477 mOsmol/kg, the chloride concentration was 94.0 mM, and the fosfomycin/tobramycin ratio was 7:3.

EXAMPLE 4

Preparation of an 8:2 Fosfomycin/Tobramycin Solution from Commercial Tobramycin for Inhalation Solution (TOBI) and Lyophilized (dry) Fosfomycin Disodium (FOSFO)

3.1665 g of fosfomycin disodium (FOSFO, 2.4002 g of fosfomycin free acid) was dissolved in two 5 mL (60 mg/mL) ampoules of Tobramycin Solution for Inhalation (TOBI, 600 mg of tobramycin base) plus 40 mL water. The initial pH of the solution was 7.50. To the solution was added 667 μl of 4.5 M NaCl. The combined solution was diluted to 100 mL with water. The final formulation had the following properties; pH 7.49, osmolality 502 mOsmol/kg, chloride concentration 33.8 mM, and the fosfomycin/tobramycin ratio was 8:2, and drug concentration of 24 mg/mL fosfomycin and 6 mg/mL of tobramycin.

Examples 5-10 set forth the procedures that have been used to generate the date presented in the Tables and Figures of this application.

EXAMPLE 5

Determination of Minimal Inhibitory Concentrations (MIC)

The efficacy of antibiotics and antibiotic combinations against Gram-positive and Gram-negative bacteria representative of species that cause respiratory infections in patients with cystic fibrosis, bronchiectasis, sinusitis, and ventilator-associated pneumonia were evaluated in MIC assays. *P. aeruginosa* strains were isolated from lung sputum samples collected from cystic fibrosis patients, blood cultures, respiratory tract infections, and skin or soft tissue infections. *E. coli, H. influenzae, B. cepacia, S. maltophilia, K. pneumoniae, M. catarrhalis, S. aureus, S. pneumoniae, S. pyogenes*, and *E. faecalis* were isolated from respiratory tract infections. *E. coli* ATCC 25922, *P. aeruginosa* ATCC 27853, and *S. aureus* ATCC 29213 were used as quality control stains.

Method A:

The MICs of fosfomycin alone, tobramycin alone, or combinations of fosfomycin plus tobramycin were determined by the agar-plate dilution method according to NCCLS guidelines (NCCLS, 2003). Bacterial strains were streaked onto Trypic Soy Agar plates (PML Microbiologicals, Wilsonville, Oreg.) containing 5% defibrinated sheep blood (hereafter referred to as blood agar plates) and incubated overnight at 35° C. Two to three bacterial colonies from the overnight cultures were inoculated into 3 mL of sterile normal saline, vortexed briefly, and adjusted to a 0.5 McFarland standard (NCCLS, 2003). The bacterial suspension was diluted 1:40 in sterile normal saline and served as the inoculum. Mueller-Hinton agar plates (hereafter referred to as MHA) were prepared by combining 16 g of agarose (Becton-Dickinson, Sparks, Md.), 22 g of Mueller-Hinton broth powder (Becton-Dickinson, Sparks, Md.), and adjusted to 1 L with distilled water. The agar was sterilized by autoclaving, cooled to 55° C., and supplemented with 25 µg/mL of glucose-6-phosphate (Sigma-Aldrich, St. Louis, Mo.). Twenty-five mL of cooled agar was aliquoted into 50 mL conical tubes and supplemented with appropriate concentrations of antibiotic to achieve concentrations ranging from 0.06 µg/mL to 512 µg/mL. After gently mixing the agar and antibiotic, the suspension was poured into sterile 100 mm petri dishes and allowed to solidify at room temperature. The antibiotic agar plates were inoculated with approximately $2\times10^4$ CFU/spot with a 48-point inoculator (Sigma-Aldrich, St. Louis, Mo.). The MIC was defined as the lowest concentration of antibiotic(s) that prevented visible growth after incubation for 18-20 hours at 35° C. The efficacy of a particular antibiotic or antibiotic combination on large populations of *P. aeruginosa* was determined by calculating the $MIC_{50}$ and $MIC_{90}$ values. The $MIC_{50}$ value was defined as the concentration of antibiotic(s) which inhibited 50% of the *P. aeruginosa* strains. The $MIC_{90}$ value was defined as the concentration of antibiotic(s) which inhibited 90% of the *P. aeruginosa* strains (Wiedemann and Grimm, 1996).

Method B:

The MICs of fosfomycin alone, tobramycin alone, or combinations of fosfomycin plus tobramycin were determined for *P. aeruginosa* strains in the presence of porcine gastric mucin to evaluate the effect of mucin and protein binding on antibiotic activity. Methodologies were identical to that described in Example 5, Method A, with the exception that 2% (weight/volume) porcine gastric mucin (Sigma Chemical Co., St. Louis, Mo.) was added to the MHA prior to autoclaving.

Method C:

The MICs of amikacin, arbekacin, dibekacin, gentamicin, kanamycin, netilimicin, neomycin, streptomycin, and tobramycin alone were determined for *P. aeruginosa* ATCC 27853 by the broth-microdilution method according to NCCLS standards (NCCLS, 2003). *E. coli* ATCC 25922 and *S. aureus* ATCC 29213 were used as quality control stains. Bacterial strains were streaked onto blood agar plates, and incubated at 35° C. for 18 hours. Two to three bacterial colonies from the overnight cultures were inoculated into 3 mL of sterile normal saline, vortexed briefly, and adjusted to a 0.5 McFarland standard (NCCLS, 2003). The bacterial suspension was diluted 1:100 in cation-adjusted Mueller-Hinton broth (hereafter referred to as CAMHB). Fifty microliters of bacterial inoculum (approximately $2\times10^5$ CFU/mL) was pipeted into individual wells of 96-well plates containing 50 µl of CAMHB (Remel, Lenexa, Kanas) supplemented with 2-fold dilutions of antibiotics ranging in concentration from 0.125 µg/mL to 128 µg/mL. The MIC was defined as the lowest concentration of antibiotic (s) that prevented visible growth after incubation at 35° C. for 18-24 hours.

EXAMPLE 6

Checkerboard Synergy

Potential interactions between fosfomycin and amikacin, arbekacin, dibekacin, gentamicin, kanamycin B, neomycin, netilimicin, streptomycin, or tobramycin were determined by the checkerboard method (Eliopoulos and Moellering, 1996). Two-fold serial dilutions of fosfomycin and aminoglycosides, which bracketed the expected MIC value for both compounds, were evaluated. Bacterial strains were streaked onto blood agar plates and incubated at 35° C. for 18-24 hours. Two to three bacterial colonies from the overnight cultures were inoculated into 3 mL of sterile normal saline, vortexed briefly, and adjusted to a 0.5 McFarland standard (NCCLS, 2003). Fifty microliters of bacterial inoculum (approximately $2\times10^5$ CFU/mL) was pipeted into individual wells of 96-well plates containing 50 µl of CAMHB supplemented with 2-fold dilutions of the two antibiotics of interest. The fractional inhibitory concentration (FIC) was calculated as the MIC of compound #1 in combination with a second compound, divided by the MIC of compound #1 alone. A summation of FIC (SFIC) was calculated for each drug combination as the sum of the individual FICs of compound #1 and #2. The FIC was calculated as the lowest concentration of antibiotics that that prevented visible growth after incubation at 18-20 hours at 35° C. Synergy was defined as an SFIC of 0.5, indifference as an SFIC >0.5 and <4, and antagonism as an SFIC >4. The lowest SFIC was used for final interpretation of drug interactions.

EXAMPLE 7

Determination of Time-Kill Kinetics

Time-kill experiments were performed in the presence of 2% porcine gastric mucin to evaluate the effect of mucin and protein binding on antibiotic activity. Two to three bacterial colonies were inoculated into 10 mL CAMHB and incubated at 35° C. in a shaking water bath (250 rpm) for 18-24 hours. A 1:40 dilution of the overnight culture was made in 10 mL of fresh CAMHB and incubated at 35° C. in a shaking water bath (250 rpm) for 1-2 hours. The resulting culture was adjusted to a 0.5 McFarland standard (NCCLS, 2003). To reduce variability in the bacterial inoculum size when comparing multiple antibiotics, one master tube of CAMHB containing 2% (weight/volume) of porcine gastric mucin was inoculated with a 1:200 dilution of bacterial inoculum (approximately $5\times10^5$ CFU/mL), supplemented with 25 µg/mL of glucose-6-phosphate, and briefly vortexed. Ten milliliter aliquots were then pipeted into 50 mL conical tubes. Fosfomycin alone, tobramycin alone, and combinations of fosfomycin plus amikacin, arbekacin, dibikacin, gentamicin, kanamycin, netilimicin, neomycin, streptomycin, or tobramycin were added to the culture medium at concentrations equal to 1, 2, 4, and 8-fold multiples of the fosfofomycin MIC (4 µg/mL) for *P. aeruginosa* ATCC 27853. The killing activity of fosfomycin plus amikacin, arbekacin, dibikacin, gentamicin, kanamycin, netilimicin, neomycin, streptomycin, or tobramycin were also compared to the killing activity of their individual components alone. For example, 32 µg/mL of a 9:1 fosfomycin:tobramycin combination was compared to killing activity of 28.8 µg/mL of fosfomycin alone and 3.2 µg/mL of tobramycin alone. A no drug control was run in each experiment. Cultures were incubated with antibiotic at 35° C. in a shaking (250 rpm) water bath for 24 hours. Bacterial killing was determined at 0, 1, 2, 4, 6, and 24 hours by making 10-fold serial dilutions of the cultures in sterile normal saline, and spreading 100 µl aliquots on blood agar plates. Culture plates were incubated at 35° C. for 18-24 hours and the number of colonies enumerated manually. The limit of detection for the colony counting method was 1 $Log_{10}$). Time-kill curves were constructed by plotting the $Log_{10}$ number of CFU/mL culture versus time. Antibiotic concentrations that reduced the original inoculum by ≥3 $Log_{10}$ CFU/mL were considered bactericidal, and concentrations that reduced the original inoculum by ≤2 $Log_{10}$ CFU/mL were defined as bacteriostatic (NCCLS, 1999). Synergism was defined as a reduction of bacterial colony counts of ≥2 $Log_{10}$ CFU/mL with the antibiotic combinations compared to the most active single antibiotic (NCCLS, 1999).

EXAMPLE 8

Determination of Minimal Bactericidal Concentration (MBC)

The MBCs of fosfomycin, amikacin, arbekacin, dibikacin, gentamicin, kanamycin B, netilimicin, neomycin, streptomycin, or tobramycin alone for *P. aeruginosa* ATCC 27853, *E. coli* ATCC 25922, and *S. aureus* ATCC 29213 were determined by the broth microdilution method according to NCCLS standards (NCCLS, 1999). Bacterial strains were streaked onto blood agar plates and incubated at 35° C. for 18-24 hours. Two to three bacterial colonies from the overnight cultures were inoculated into 3 mL of sterile normal saline, vortexed briefly, and adjusted to a 0.5 McFarland standard (NCCLS, 2003). Fifty microliters of bacterial inoculum (approximately $2\times10^5$ CFU/mL) was pipeted into individual wells of 96-well plates containing 50 µl of CAMHB (Remel, Lenexa, Kanas) supplemented with 2-fold dilutions of antibiotics ranging in concentration from 0.125 µg/mL to 128 µg/mL. Plates were incubated at 35° C. for 18-24 hours and MIC determined as described in Example 5, Method C. The contents of wells showing no growth (MIC and above) were mixed with a pipetor and duplicate 10 µl samples spread onto blood agar plates. Culture plates were incubated at 35° C. for 18-24 hours and the number of bacterial colonies on each plate enumerated manually. Rejection values were determined by NCCLS methods which considers the final inoculum size, single or double sampling, pipetting error, and the Poisson distribution of sample responses (NCCLS, 1999). For example, if the final inoculum was $5\times10^5$ CFU/mL and duplicate samples were evaluated, the lowest dilution having fewer than a total of 25 colonies was considered the MBC. The MBC was defined as the ≥3 $Log_{10}$ decrease in CFU/mL of the original inoculum as described by NCCLS standards (NCCLS, 1999). The MBC/MIC ratios were calculated by dividing the MBC by the MIC.

EXAMPLE 9

Determination of Frequency of Single-Step Resistance

The frequency of single-step spontaneous resistance mutation was determined for 5 susceptible *P. aeruginosa* strains. The bacterial inoculum was prepared by inoculating 5 mL of CAMHB with 2-3 bacterial colonies and incubating at 35° C. in a shaking water bath (250 rpm) for 18 h. A 1:20 dilution of the overnight culture was made into 50 mL of fresh CAMHB in a 125 ml erlenmyer flask and incubated at 35° C. in a shaking waterbath (250 rpm) for 8 hours. Cultures were centrifuged at 2,500 rpm, room temperature, for 20 min. The supernatant was decanted off and the cell pellet from the 50 mL of culture resuspended in 500 µl-1000 µl CAMHB. The CFU/mL in the bacterial suspension was determined by making 10-fold serial dilutions in sterile normal saline, and spreading 100 µl aliquots on blood agar plates. Culture plates were incubated at 35° C. for 18-24 hours and the number of colonies enumerated manually. One hundred microliters of bacterial cell suspension (approximately $10^9$ CFU) was spread onto MHA plates containing 128 µg/mL of fosfomycin, 8 µg/mL of tobramycin, or 128 µg/mL of fosfomycin plus 8 µg/mL of tobramycin. The culture plates were incubated at 35° C. for 48-72 hours and the number of colonies on each plate was enumerated manually. The frequency of resistance was calculated by dividing the number of bacteria growing at the defined antibiotic concentration by the number of bacteria in the original inoculum. Representative mutants were evaluated for changes in MIC to fosfomycin alone, tobramycin alone, and fosfomycin plus tobramycin combinations as described in Example 5, Method A.

EXAMPLE 10

Multistep Resistance Analysis

Development of resistance during continuous serial passage was evaluated with a clinical *P. aeruginosa* strain susceptible to fosfomycin (MIC-8 µg/mL) and tobramycin (MIC=0.5 µg/mL). A single colony of *P. aeruginosa* COR-014 was inoculated into 5 mL of MHCAB and briefly vortexed. Two-fold serial dilutions of fosfomycin alone covering the range of 1 µg/mL-512 µg/mL, tobramycin alone covering 0.0625 µg/mL-512 µg/mL, and a 9:1 fosfomycin:tobramycin combination covering 0.0625 µg/mL-512 µg/mL were made in CAMHB. Ten microliters of bacterial suspension was pipetted into 3 mL of each antibiotic dilution and incubated statically at 35° C. for 18-24 hours. Tubes with the highest concentration of antibiotic having visible bacterial growth were selected from each antibiotic dilution series and 100 µl of the culture was pipeted into a fresh antibiotic dilution series. Tubes were incubated statically at 35° C. for 18-24 hours. This process was repeated for a total of 28 times. MICs of fosfomycin alone, tobramycin alone, and fosfomycin plus tobramycin were determined for the parent strain and resistant isolates collected after each passage as described in Example 5, Method C.

EXAMPLE 11

Determination of Animal Efficacy

The in vivo efficacy of aerosolized fosfomycin alone, tobramycin alone and combinations of fosfomycin plus tobramycin were evaluated against *E. coli* ATCC 25922 and *P. aeruginosa* ATCC 27853 in rat lungs. The bacterial inoculum used to establish the rat lung infections consisted of a mixture of bacteria and agarose beads. *E. coli* ATCC 25922 or *P. aeruginosa* ATCC 27853 was streaked onto blood agar plates and incubated for 18-24 hours at 35° C. Two to three colonies were inoculated into 10 mL Tryptic Soy Broth (hereafter referred to as TSB) and incubated statically at 35° C. for 1.5 to 2 hours. The culture was adjusted to an optical density of 0.1 (625 nm) in fresh TSB and then diluted 1:5 in TSB. One milliliter of bacterial suspension (approximately $10^7$ CFU/mL) was added to 10 mL of a 2% noble agar solution and briefly mixed by inversion. The mixture was added to 150 mL of heavy white mineral oil equilibrated to 55° C. and stirred on ice for 5 minutes. The cooled suspension was poured into a 250 mL centrifuge tube and centrifuged at 3,000 rpm, 4° C., for 10 minutes. The supernatant was decanted off, the pellet resuspended in 25 mL of normal sterile saline, and transferred to a 50 mL conical centrifuge tube. Following centrifugation at 3,000 rpm, 4° C., for 10 minutes, the supernatant was decanted off and the pellet resuspended in 10 mL of saline.

The suspension was centrifuged at 3,000 rpm, 4° C., for 10 minutes and the supernatant decanted off. The pellet was resuspended in approximately 10 mL sterile normal saline and then diluted 1:30 in a sterile 2% agarose bead solution to give approximately 10-1000 CFU/mL.

Prior to intratracheal installation of the bacterial inoculum, male Sprague-Dawly rats (200-250 g) were anesthetized by exposure to isoflurane for 5 minutes. An intratracheal needle was inserted into the trachea and 80 µA of agarose beads containing approximately 10-100 CFU of *E. coli* ATCC 25922 or *P. aeruginosa* ATCC 27853 were instilled into the lungs with a 1 mL syringe. The rats were placed into individual cages and allowed to recover for approximately 18 hours.

Fosfomycin alone, tobramycin alone, and fosfomycin:tobramycin combinations were administered to rats using an aerosol exposure device (In Tox Products, New Mexico). The system consisted of a central chamber having separate aerosol supply and exhaust paths. The central chamber had 24 ports that were directly connected to the aerosol supply system. Rats were placed into individual aerosol exposure tubes and restrained with an adjustable push plate and end cap assembly so they could not turn around or back away from the end of the tube. The restraint tubes containing the rats were loaded onto ports on the central chamber and the air flow adjusted to 1 liter/min. The air (breathable quality air) flow to the PARI LC Star nebulizer was held constant at 6.9 liters per minute. Fosfomycin alone, tobramycin alone, or 9:1, 8:2, or 7:3 fosfomycin:tobramycin combinations were nebulized at 0.2 mL/min and delivered to the rats via the aerosol supply path. Additional air (hereafter referred to as dilution air) was delivered to nebulizer (where) to balance the over pressure of the air used to deliver aerosolized drugs to the rats. Rodents were exposed to aerosolized antibiotics for up to 2 hours, twice daily for 3 consecutive days. Each treatment group consisted of 5-8 animals per group. A non-treatment control was included in each experiment.

Bacterial killing was evaluated 18 hours after the last exposure. Rats were anesthetized with isoflurane and euthanized by intraperitoneal administration of 500 µl of phenobarbitol. The lungs were removed aseptically, excess tissue removed and the lung weight determined. Lungs were placed in 10 mL glass vials, and 3 mL of normal sterile saline added per gram tissue. Samples were homogenized with hand-held homogenizer for 30 seconds. Bacterial killing was determined by making 10-fold serial dilutions of the lung homogenate in sterile normal saline, and spreading 100 µl aliquots on blood agar plates. Culture plates were incubated at 35° C. for 18-24 hours and the number of bacterial colonies enumerated manually. Antibiotic efficacy was determined by comparing the CFU's/lung from the non-treatment control group to the treatment groups.

REFERENCES

Al-Aloui, M., H. Miller, S. Alapati, P. A. Stockton, M. J. Ledson, and M. J. Walshaw. 2005. Renal impairment in cystic fibrosis patients due to repeated intravenous aminoglycoside use. Ped. Pulmon. 39:15-20.

Ansorg, R., K.-D. Muller, and W. Wiora. 1990. Comparison of inhibitory and bactericidal activity of antipseudomonal antiotics against *Pseudomonas aeruginosa* isolates from cystic fibrosis patients. Chemother. 36:222-229.

Arca, P., G. Reguera, and C. Hardisson. 1997. Plasmid-encoded fosfomycin resistance in bacteria isolated from the urinary tract in a multicentre survey. J. Antimicrob. Chemother. 40:393-399.

Bacardi, R., J. Tomos, I. Moga, N. Marti, P. Alomar, L. Gaztelurrutia, and C. Villalonga. 1977. Treatment of respiratory infections with fosfomycin. Chemother. 23 (Suppl. 1):343-347.

Bonora, V., C. Lozano, M. Santos, M. Paz, J. Baguena, and M. Gobernado. 1977. Fosfomycin in treatment of respiratory bacterial infections. Chemother 23 (Suppl. 1):337-341.

Conway, S. P. 2005. Nebulized antibiotic therapy: the evidence. Chronic Respir. Dis. 2:35-41.

Conway, S P., K G Brownlee, M Denton, and D G Peckham. 2003. Antibiotic treatment of multidrug-resistant organisms in cystic fibrosis. Am J Respir Med 2(4):321-332.

Craig, W. A. 1998. Pharmacokinetic/pharmacodynamic parameters: rationale for antibacterial dosing of mice and men. Clin. Infect. Dis. 26 (1):1-12.

Forsgren, A. and M. Walder. 1983. Antimicrobial activity of fosfomycin in vitro. J. Antimicrob. Chemother. 11(5):467-471.

Flume, P. and M. E. Klepser. 2002. The rationale for aerosolized antibiotics. Pharmacotherapy 22 (3 Pt 2):71S-79S.

Geller, D. E., W. H. Pitlick, P. A. Nardella, W. G. Tracewell, and B. W. Ramsey. 2002. Pharmacokinetics and bioavailability of aerosolized tobramycin in cystic fibrosis. Chest. 122:219-226.

Gibson, R L., J L Burns, and B W Ramsey. 2003. Pathophysiology and management of pulmonary infections in cystic fibrosis. Am. J. Respir. Crit. Care. Med. 168(8):918-951.

Greenwood, D., J. Brown, and R. Edwards. 1992. The influence of anaerobiosis on the activity fosfomycin tromtamol. Infection. 20(4):S305-S309.

Grif, K., M. P. Dierich, K. Pfaller, P. A. Miglioli, and F. Allerberger. 2001. In vitro activity of fosfomycin in combination with various antistaphylococcal substances. J Antimicrob Chemother 48:209-217.

Grimm, H. 1979. In vitro investigations with fosfomycin on Mueller-hinton agar with and without glucose-6-phosphate. Infect. 7(4):256-259.

Hammett-Stabler, C. A. and T. Johns. 1998. Laboratory guidelines for monitoring of antimicrobial drugs. Clin. Chem. 44(5):1129-1140.

Honorato, J., R. R. P. Ortola, R. Masso, and J. M. Reparaz. 1977. fosfomycin in acute bronchopneumonopathies. Chemother 23 (Suppl. 1):331-336.

Hunt, B. E., A. Weber, A. Berger, B. Ramsey, and A. L. Smith. 1995. Macromolecular mechanisms of sputum inhibition of tobramycin activity. Antimicrob. Agents. Chemother. 39(1):34-39.

Kahan, F. M., J. S. Kahan, P. J. Cassidy, and H. Kropp. 1974. The mechanism of action of fosfomycin (phoshonomycin). Ann N Y Acad Sci 253:364-386.

Katznelson, D., Y. Yahev, and E. 1984. Rubinstein. Fosfomycin in the treatment of cystic fibrosis. Eur J Clin Microbiol 3(3):213.

Kamijyo, A., Z. Matsuzaki, K. Kikushima, J. Ogino, I. Nozawa, T. Matsuoka, S. Endo, and Y. Okamoto. 2001. Fosfomycin nebulizer therapy to chronic sinusitis. Auris. Nasus. Larynx. 28(3):227-232.

Kondo, H., K. Suzuki, I. Takagi, N. Miyamoto, S. Baba, T. kobayashi, A. Yokota, I. Tanaka, and K. Sugiyama. 1996. Transitional concentration of antibacterial agent to the maxillary sinus via a nebulizer. Acta Otolaryngol (Stockh) Suppl 525:64-67.

Mirakhur, A., M. J. Gallagher, M. J. Ledson, C. A. Hart, and M. J. Walshaw. 2003. Fosfomycin therapy for multiresistant *Pseudomonas aeruginosa* in cystic fibrosis. J Cystic Fibrosis 2:19-24.

Kuhn, R. J. 2001. Formulation of aerosolized therapeutics. Chest. 120:94 S-98S.

Lang, B. J., S. D. Aaron, W. Ferris, P. C. Herbert, and N. E. MacDonald. 2000. Multiple combination bactericidal antibiotic testing for patients with cystic fibrosis infected with multiresistant strains of *Pseudomonas aeruginosa*. Am. J. Respir. Crit. Care. Med. 162:2241-2245.

Marchese, A., L. Gualco, E. A. Debbia, G. C. Schito, and A. M. Schito. 2003. In vitro activity of fosfomycin against gram-negative urinary pathogens and the biological cost of fosfomycin resistance. Int. J. Antimicrob. Agents. 22(2): 53-59.

Mendelman, P. M., A. L. Smith, J. Levy, A. Weber, B. Ramsey, and R. L. Davis. 1985. Aminoglycoside penetration, inactivation, and efficacy in cystic fibrosis sputum. Am. Rev. Respir. Dis. 132(4):761-765.

Menendez, A., A. Tutor, and A. S. Sousa. 1977. Treatment of respiratory infections with fosfomycin. Chemother 23 (Suppl. 1):348-357.

Mingeot-Leclercq, M-P. and P. M. Tulkens. 1999. Aminoglycosides: Nephrotoxity. Antimicrob. Agents. Chemother. 43(5):1003-1012.

Mirakhur, A., M. J. Gallagher, M. J. Ledson, C. A. Hart, and M. J. Walshaw. 2003. Fosfomycin therapy for multiresistant *Pseudomonas aeruginosa* in cystic fibrosis. J. Cyst fibros. 2(1):19-24.

Moreno, S., C. Ezpeleta, F. Parras, C. Banos, J. Martinez Beltran, and L. Buzon. 1986. Cure of a case of *Haemophilus aphrophilus* endocarditis with a combination of fosfomycin and gentamicin. J. Antimicrob. Chemother. 18(6): 771-772.

Mueller, M., A. de la Pena, and H. Derendorf. 2004. Issues in pharmacokinetics and pharmacodynamics of anti-infective agents: kill curves versus MIC. Antimicrob. Agents. Chemother. 48(2):369-377.

National Committee for Clinical Laboratory Standards (NCCLS). 2003. Methods for dilution antimicrobial susceptibility tests for bacteria that grows aerobically; approved standard. M7-A6, Vol. 23 No. 2. National Committee for clinical Laboratory Standards, Wayne, Pa.

National Committee for Clinical Laboratory Standards (NCCLS). 1999. Methods for determining bactericidal activity of antimicrobial agents; approved guideline. M26-A, Vol. 19 No. 18. National Committee for clinical Laboratory Standards, Wayne, Pa.

Nilsson, A. I., O. G. Berg, O. Aspevall, G. Kahlmeter, and D. I. Andersson. 2003. Biological costs and mechanisms of fosfomycin resistance in *Escherichia coli*. Antimicrob. Agents. Chemother. 47(9):2850-2858.

O'Riordan, T. G. 2000. Inhaled antimicrobial therapy: from cystic fibrosis to the flu. Respir. Care. 45(7):836-845.

Perri, M. B., E. Hershberger, M. Ionescu, C. Lauter, and M. J. Zervos. 2002. In vitro susceptibility of vancomycin-resistant enterococci (VRE) to fosfomycin. Diagn. Microbiol. Infect. Dis. 42:269-271.

Pitt, T L., M Sparrow, M Warner, and M Stefanidou. 2005. Survey of resistance of *Pseudomonas aeruginosa* from UK patients with cystic fibrosis to six commonly prescribed antimicrobial agents. Thorax 58(9):794-796.

Ramphal, R., M. Lhermitte, M. Filliat, and P. Roussel. 1988. The binding of antipseudomonal antibiotics to macromolecules from cystic fibrosis sputum. J. Antimicrob. Chemother. 22:483-490.

Ramsey, B W., M S Pepe, J M Quan, K L Otto, A B Montgomery, J Williams-Warren, K M Vasiljev, D Borowitz, C M Bowman, B C Marshall, S Marshall, and A L Smith. 1999. Intermittent administration of inhaled tobramycin in patients with cystic fibrosis. Cystic fibrosis inhaled tobramycin study group. N Engl J Med 340(1):23-30.

Ramsey B W. 1996. Management of pulmonary disease in patients with cystic fibrosis. N Engl J Med 335(3):179-188.

Ramsey, B W., H L Dorkin, J D Eisenberg, R L Gibson, I R Harwood, R M Kravitz, D V Schidlow, R W Wilmott, S J Astley, M A McBuurnie 1993. Efficacy of aerosolized tobramycin in patients with cystic fibrosis. N Engl J Med 328(24):1740-1746.

Reeves, D. S. 1994. Fosfomycin trometamol. J Antimicrob Chemother 34:853-858.

Schulin, T. 2002. In vitro activity of the aerosolized agents colistin and tobramycin and five intravenous agents against *Pseudomonas aeruginosa* isolated from cystic fibrosis patients in southwestern Germany. J Antimicrob Chemother 49:403-406.

Shawar, R M., D L MacLeod, R L Garber, J L Burns, J R Stapp, C R Clausen, and S K Tanaka. 1999. Activities of tobramycin and six other antibiotics against *Pseudomonas aeruginosa* isolates from patients with cystic fibrosis. Antimicrob Agents Chemother. 43(12):2877-2880.

Smith, A. L., C. Doersbuk, D. Goldman, E. Gore, B. Hilman, M. Marks, R. Moss, B. Ramsey, G. Redding, T. Rubio, J. Williams-Warren, R. Wilmott, H. D. Wilson, and R. Yogev. 1999. Comparison of a β-lactam alone versus β-lactam and an aminoglycoside for pulmonary exacerbations in cystic fibrosis. J. Pediatr. 134:413-421.

Spencker, F. B., L. Staber, T. Lietz, R. Schille, and A. C. Rodloff. 2002. Development of resistance in *Pseudomonas aeruginosa* obtained from patients with cystic fibrosis at different times. Clin. Microbiol. Infect. 9:370-379.

Tan, K. V., M. Mulheran, A. J. Knox, and A. R. Smyth. 2003. Aminoglycoside prescribing and surveillance in cystic fibrosis. Am. J. Respir. Crit Care med. 167(6):819-823.

Van Eldere, J. 2003. Multicenter surveillance of *Pseudomonas aeruginosa* susceptibility patterns in nosocomial infections. J. Antimicrob. Chemother. 51:347-352.

Vakulenko, S. B. and S. Mobashery. 2003. Versatility of aminoglycosides and prospects for their future. Clin. Microbiol. Rev. 16(3):430-450.

Weiss, K., and J. R. Lapointe. 1995. Routine susceptibility testing of four antibiotic combinations for improvement of laboratory guide to therapy of cystic fibrosis infections caused by *Pseudomonas aeruginosa*. Antimicrob. Agents. Chemother. 39(11):2411-2414.

Woodruff, H. B., J. M. Mata, S. Hernandez, S. Mochales, A. Rodriguez, E. O. Stapley, H. Wallick, A. K. Miller and D. Hendlin. 1977. Fosfomycin: Laboratory studies. Chemother. 23(1):1-22)

We claim:

1. An aerosol formulation for the treatment of infection caused by bacteria in the respiratory tract of a patient
said formulation comprising from about 1 mg to about 300 mg of fosfomycin, and about 1 mg to about 300 mg of tobramycin; wherein
said formulation is to be administered by a nebulizer, and wherein the weight ratio of fosfomycin to tobramycin is selected from the group consisting of: (i) from about 7 parts by weight of fosfomycin to about 3 parts by weight of tobramycin; (ii) from about 8 parts by weight of fosfomycin to about 2 parts by weight of tobramycin; and (iii) from about 9 parts fosfomycin to about 1 part by weight of tobramycin.

2. The aerosol formulation of claim 1 wherein said formulation is packaged in a dual blow-fill seal ampoule such that each antibiotic is individually formulated in water and pH adjusted such that the fosfomycin solution has a pH between 8-13 and the tobramycin solution has a pH between 1-6 and, when the dual ampoule is opened and the contents reconstituted, the resulting solution has a pH between about 4.5 and 8.0, and wherein said physiologically suitable solution comprises from about 0.5 to about 7 ml of solution containing a chloride concentration >30 mM.

3. The aerosol formulation of claim 1 wherein the weight ratio of fosfomycin to tobramycin is from about 9 parts by weight of fosfomycin to about 1 part by weight of tobramycin.

4. The aerosol formulation of claim 1 wherein the weight ratio of fosfomycin to tobramycin is from about 7 parts by weight of fosfomycin to about 3 parts by weight of tobramycin.

5. The aerosol formulation of claim 1 wherein the weight ratio of fosfomycin to tobramycin is about 8 parts fosfomycin to about 2 parts tobramycin.

6. A method for the treatment of infections of the respiratory tract caused by bacteria comprising administering to a patient in need of such treatment the aerosol formulation of claim 1.

7. The method of claim 6 wherein said formulation has a pH between about 4.5 and 8.0 in water with a chloride concentration >30 mM.

8. The method of claim 6 wherein said formulation is administered by aerosolization using a jet, ultrasonic, pressurized or vibrating porous plate nebulizer or other device capable of delivering the formulation to the nasal passages or pulmonary airway and the aerosol has with a particle size distribution predominately between 1 and 5 μm.

9. The method of claim 6 wherein the infections are *P. aeruginosa* or *S. aureus*.

10. The method of claim 6 wherein the infections are selected from the group consisting of bacterial sinucitis, cystic fibrosis, pulmonary *Pseudomonas*, pneumonia and ventilator associated pneumonia.

11. A method for the treatment of infections of the respiratory tract caused by the bacteria *P. aeruginosa* comprising administering to a patient in need of such treatment the aerosol formulation of claim 1.

12. A reconstituted solution of about 1 to about 300 mg of fosfomycin and about 1 to about 300 mg tobramycin of the formulation of claim 1.

* * * * *